(12) United States Patent
Timmers et al.

(10) Patent No.: US 8,071,589 B2
(45) Date of Patent: Dec. 6, 2011

(54) DIHYDROBENZOINDAZOLES

(75) Inventors: Cornelis Marius Timmers, Oss (NL); Hubert Jan Jozef Loozen, Oss (NL)

(73) Assignee: N. V. Organon, Oss (NL)

( * ) Notice: Subject to any disclaimer, the term of this patent is extended or adjusted under 35 U.S.C. 154(b) by 0 days.

(21) Appl. No.: 12/845,813

(22) Filed: Jul. 29, 2010

(65) Prior Publication Data

US 2011/0028451 A1 Feb. 3, 2011

Related U.S. Application Data

(60) Provisional application No. 61/230,217, filed on Jul. 31, 2009.

(51) Int. Cl.
| | |
|---|---|
| C07D 243/00 | (2006.01) |
| C07D 487/00 | (2006.01) |
| A61K 31/55 | (2006.01) |
| A61K 31/415 | (2006.01) |
| A61P 5/06 | (2006.01) |

(52) U.S. Cl. ...... 514/218; 514/406; 540/492; 548/359.1
(58) Field of Classification Search .................. 540/492; 514/218, 406; 548/359.1
See application file for complete search history.

*Primary Examiner* — Bruck Kifle
(74) *Attorney, Agent, or Firm* — Janet E. Fair; John C. Todaro

(57) ABSTRACT

The invention relates to benzoindazole derivatives according to general Formula I

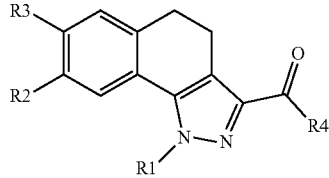

Formula 1 or a pharmaceutically acceptable salt thereof. The compounds can be used for the treatment of infertility.

11 Claims, No Drawings

DIHYDROBENZOINDAZOLES

The present invention relates to 4,5-dihydro-1H-benzo[g] indazole derivatives, to pharmaceutical compositions comprising the same and to the use of said compounds for the manufacture of medicaments for the treatment of infertility.

Gonadotropins serve important functions in a variety of bodily functions including metabolism, temperature regulation and the reproductive process. Gonadotropins act on specific gonadal cell types to initiate ovarian and testicular differentiation and steroidogenesis. The pituitary gonadotropin FSH (follicle stimulating hormone), for example, plays a pivotal role in the stimulation of follicle development and maturation whereas LH (luteinizing hormone) induces ovulation (Sharp, R. M. *Clin Endocrinol.* 33, 787-807 (1990); Dorrington and Armstrong, *Recent Prog. Horm. Res.* 35, 301-342 (1979)). Currently, FSH is applied clinically for ovarian stimulation, i.e. controlled ovarian stimulation for in vitro fertilization (IVF) and induction of ovulation in infertile anovulatory women (Insler, V., Int. *J. Fertility* 33, 85-97 (1988), Navot and Rosenwaks, *J. Vitro Fert. Embryo Transfer* 5, 3-13 (1988)), as well as for male hypogonadism and male infertility.

The gonadotropin FSH is released from the anterior pituitary under the influence of gonadotropin-releasing hormone and estrogens, and from the placenta during pregnancy. In the female, FSH acts on the ovaries promoting development of follicles and is the major hormone regulating secretion of estrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity (Morse et al, *Amer. J. Reproduct. Immunol. and Microbiology* 17, 143 (1988)). Alternatively, they can be prepared as recombinant gonadotropins. Recombinant human FSH is available commercially and is being used in assisted reproduction (Olijve et al. *Mol. Hum. Reprod.* 2, 371-381 (1996); Devroey et al. *Lancet* 339, 1170-1171 (1992)).

The actions of the FSH hormone are mediated by a specific membrane receptor that is a member of the large family of G-protein coupled receptors. These receptors consist of a single polypeptide with seven transmembrane domains and are able to interact with the Gs protein, leading to the activation of adenylate cyclase.

The FSH receptor (FSHR) is a highly specific target in the ovarian follicle growth process and is exclusively expressed in the ovary. Low molecular weight FSHR agonists can be used for the same clinical purposes as native FSH, i.e. for the treatment of infertility and for controlled ovarian stimulation preceding in vitro fertilisation.

Certain tetrahydroquinoline derivatives have recently been disclosed in the International Application WO 2003/004028 (AKZO NOBEL N.V.) as FSHR modulating substances, either having agonistic or antagonistic properties.

Low molecular weight FSH mimetics with agonistic properties were disclosed in the International Application WO 2000/08015 (Applied Research Systems ARS Holding N.V.); WO 2004/031182 (Applied Research Systems ARS Holding N.V.); WO 2002/09706 (Affymax Research Institute); WO 2005/087765 (Arena Pharmaceuticals, Inc); WO 2006/117368 (AKZO NOBEL N.V.); WO 2006/117370 (AKZO NOBEL N.V.); WO 2006/117371 (AKZO NOBEL N.V.) and in WO 2006/117023 (AKZO NOBEL N.V.).

There clearly is a need for low molecular weight hormone mimetics that selectively activate the FSH receptor.

To that aim, the present invention provides dihydrobenzoindazoles derivatives.

More specifically, the present invention provides dihydrobenzoindazole compounds according to Formula I

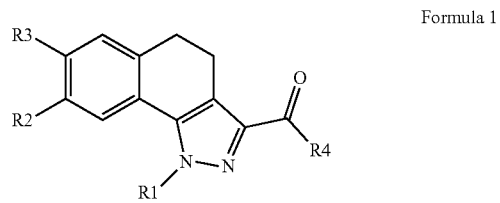

Formula 1

In this formula the R groups have the following definitions:
R1 is phenyl, optionally substituted with halogen, nitro, (1-6C)alkyl, (2-6C)alkenyl, (1-6C)alkoxy, (2-5C)hetero aryl, (3-6C)cycloalkyl; or
R1 is (2-5C)heteroaryl, optionally fused with a benzo group and optionally substituted at the heteroaryl or benzo group with halogen or (1-4C)alkyl; or
R1 is (2-5C)heterocycloalkyl or (2-5C)heterocycloalkenyl, both optionally substituted with one or more fluorines, (1-2C) alkyl groups or (1-3C)alkoxy groups.
R2 is (1-6C)alkyl, (2-6C)alkenyl, (2-6C)alkynyl, (1-6C) alkoxy, (2-5C)heteroaryl, R5-carbonylamino, R5-aminocarbonyl or (1-4C)alkylsulfonamino. All alkyl groups in R2 may be optionally substituted with one or more hydroxyl groups or fluorines.
R3 is (1-6C)alkoxy or hydroxyl.
R4 is (di)[(1-6C)alkyl]amino; or R4 is pyrrolidin-1-yl, optionally substituted with one or more (1-2C)alkyl groups; or R4 is diazacycloheptyl, optionally substituted with (1-6C) alkylcarbonyl or (3-6C)cycloalkylcarbonyl; or
R4 is

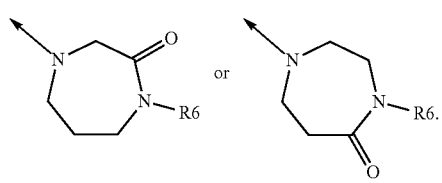

R5 is (2-5C)heteroaryl or (1-6C)alkyl, both optionally substituted with one or more hydroxyl groups or halogens; or
R5 is (2-5C)heterocycloalkyl(1-4C)alkyl, the heterocycloalkyl group optionally substituted with (1-4C)alkyl or (di) [(1-4C)alkyl]amino(1-4C)alkyl.
R6 is (1-6C)alkyl.

The dihydrobenzoindazole compounds according to the present invention are potent FSH receptor activators and can be used for the same clinical purposes as native FSH since they behave like agonists, with the advantage that they may be prepared synthetically, may display altered stability properties and may be administered differently.

Thus, the FSH receptor agonists of the present invention may be used for the treatment of fertility disorders e.g. controlled ovarian stimulation and IVF procedures.

The term (1-4C)alkyl as used in the definition means a branched or unbranched alkyl group having 1-4 carbon atoms, being methyl, ethyl, n-propyl, isopropyl, n-butyl, isobutyl, sec-butyl and tert-butyl.

The term (1-2C)alkyl as used in the definition means an alkyl group having 1-2 carbon atoms, being methyl or ethyl.

The term (1-6C)alkyl means a branched or unbranched alkyl group having 1-6 carbon atoms, for example methyl, ethyl, n-propyl, isopropyl, n-butyl, tert-butyl, n-pentyl and n-hexyl. (1-5C)Alkyl groups are preferred, (1-4C)alkyl being the most preferred.

The term (2-6C)alkenyl means a branched or unbranched alkenyl group having 2-6 carbon atoms, such as ethenyl, 2-butenyl, and n-pentenyl.

The term (2-6C)alkynyl means a branched or unbranched alkynyl group having 2-6 carbon atoms, such as ethynyl, propynyl and n-pentynyl.

The term (1-6C)alkoxy means an alkoxy group having 1-6 carbon atoms, the alkyl moiety having the same meaning as previously defined. (1-3C)Alkoxy groups are preferred.

The term (1-4C)alkoxy means an alkoxy group having 1-4 carbon atoms, the alkyl moiety having the same meaning as previously defined.

The term (1-3C)alkoxy means an alkoxy group having 1-3 carbon atoms, the alkyl moiety having the same meaning as previously defined.

The term (2-5C)heteroaryl means an aromatic group having 2-5 carbon atoms and 1-3 heteroatoms selected from N, O and S, like imidazolyl, thiadiazolyl, pyridinyl, thienyl or furyl. Preferred heteroaryl groups are thienyl, thiazolyl, furyl and pyridinyl. The (2-5C)heteroaryl group may be attached via a carbon atom or a nitrogen, if feasible. N-containing heteroaryl groups include their corresponding N-oxide derivatives where appropriate.

The term (1-4C)alkylsulfonamino means a alkylsulfonamino group, the alkyl group of which contains 1-4 carbon atoms with the same meaning as previously defined.

The term (di)[(1-6C)alkyl]amino as used herein means an amino group, monosubstituted or disubstituted with alkyl group(s), each containing 1-6 carbon atoms and having the same meaning as previously defined.

The term (di)[(1-4C)alkyl]amino as used herein means an amino group, monosubstituted or disubstituted with alkyl group(s), each containing 1-4 carbon atoms and having the same meaning as previously defined.

The term (di)(1-4C)alkylamino(1-4C)alkyl as used herein means a (di)alkylamino group, the alkyl group(s) of which each contain(s) 1-4 carbon atoms with the same meaning as previously defined, connected via the amino group to an alkyl group which contains 1-4 carbon atoms with the same meaning as previously defined.

The term (1-6C)alkylcarbonyl means an alkylcarbonyl group, the alkyl group of which contains 1-6 carbon atoms with the same meaning as previously defined.

The term (3-6C)cycloalkyl means a cycloalkyl group having 3-6 carbon atoms, such as cyclopropyl, ethylcyclopropyl, cyclobutyl, methylcyclobutyl, cyclopentyl and cyclohexyl.

The term (3-6C)cycloalkylcarbonyl means a cycloalkylcarbonyl group, the cycloalkyl group of which contains 3-6 carbon atoms with the same meaning as previously defined.

The term (2-5C)heterocycloalkyl means a heterocycloalkyl group having 2-5 carbon atoms, preferably 3-5 carbon atoms, including 1-3 heteroatoms selected from N, O and/or S, which may be attached via a nitrogen if feasible, or a carbon atom. Preferred number of heteroatoms is one or two. Most preferred are azacyclobutyl, morpholinyl, pyrazinyl, tetrahydro-2H-pyran-4-yl and tetrahydro-2H-thiopyran-4-yl. Preferred heteroatoms are N or O The term (2-5C)heterocycloalkenyl means a heterocycloalkenyl group having 2-5 carbon atoms, including 1-3 heteroatoms selected from N, O and/or S, which may be attached via a nitrogen if feasible, or a carbon atom. Preferred number of heteroatoms is one or two. Preferred heterocycloalkyl groups are 3,6-dihydro-2H-pyran-4-yl and 3,6-dihydro-2H-thiopyran-4-yl.

The term (2-5C)heterocycloalkyl(1-4C)alkyl means a heterocycloalkylalkyl group, the heterocycloalkyl group of which contains 2-5 carbon atoms, preferably 3-5 carbon atoms, with the same meaning as previously defined and the alkyl group of which contains 1-4 carbon atoms with the same meaning as previously defined.

The term halogen means fluorine, chlorine, bromine or iodine.

The term "substituted" means that one or more hydrogens on the designated atom are replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

In the above definitions with multifunctional groups the attachment point is at the last group.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

In one aspect the invention relate to compounds of Formula I wherein the substituent at the alkyl groups in R2 is one or more hydroxyl.

In one aspect the invention relates to compounds of Formula I wherein R2 is (1-6C)alkoxy, (2-5C)heteroaryl, R5-carbonylamino or (1-4C)alkylsulfonamino.

The invention also relates to compounds of Formula I, wherein R2 is (1-4C)alkoxy.

In another aspect the invention relates to compounds of formula I wherein R3 is methoxy.

In yet another aspect the invention concerns compounds of Formula I wherein R4 is 1,4-diazacycloheptyl, optionally substituted at the nitrogen at position 4 with (1-6C)alkylcarbonyl or (3-6C)cycloalkylcarbonyl.

In still another aspect the invention concerns compounds of Formula I wherein R4 is di [(1-6C)alkyl]amino.

In still another aspect the invention concerns compounds of Formula I wherein R1 is phenyl, optionally substituted with halogen, nitro, (1-6C)alkyl, (2-6C)alkenyl, (1-6C)alkoxy, (2-5C)heteroaryl, (3-6C)cycloalkyl; or R1 is (2-5C)heteroaryl, optionally fused with a benzo group.

The invention also relates to compounds of Formula I, wherein R1 is phenyl, optionally substituted with halogen, nitro, (1-6C)alkyl, (2-6C)alkenyl, (1-6C)alkoxy or (3-6C)cycloalkyl or R1 is thienyl.

The invention also relates to compounds of Formula I, wherein R5 is (2-5C)heteroaryl, (2-5C)heterocycloalkyl(1-4C)alkyl, the heterocycloalkyl group optionally substituted with (1-4C)alkyl or (di)[(1-4C)alkyl]amino(1-4C)alkyl.

The invention also relates to those compounds wherein all specific definitions for R1 through R6 in the various aspects of the invention as defined previously occur in any combination within the definition of the dihydrobenzoindazole compound of Formula I.

In another aspect the invention relates to compounds according to Formula I wherein R5 is (2-5C)heteroaryl, (2-5C)heterocycloalkyl(1-4C)alkyl, the heterocycloalkyl group optionally substituted with (1-4C)alkyl or (di)[(1-4C) alkyl]amino(1-4C)alkyl.

All compounds of the invention have an $EC_{50}$ of less than 10 µM.

In another aspect the invention relates to compounds of formula I which have an $EC_{50}$ of less than 1 µM. In yet another aspect the invention relates to compounds of formula I which have an $EC_{50}$ of 100 nM or less.

The term $EC_{50}$ means the concentration of the test compound that elicits half-maximal (50%) stimulation compared to the compound's maximally attainable effect. $pEC_{50}$ is the negative log of $EC_{50}$. The values can be determined e.g. in a cell line transfected with a FSH receptor gene and cotransfected with a cAMP responsive element/promoter directing the expression of a reporter gene. For the determination a software program such as MathIQ (version 2.0, ID Business Solutions Limited) can be used.

4,5-Dihydro-1H-benzo[g]indazole-3-carboxamide derivatives according to the general structure I, in which the substituents R1-R6 are as defined previously, are available by general methods known in chemical literature (R. W. Hamilton, J. Het. Chem. 13, 545 (1976)). These methods have been applied since then for the construction of related compounds as cannabinoid antagonists, anti-inflammatory and antiproliferating agents (G. Murineddu, S. Ruiu, J-M. Mussinu, G. Loriga, G. E. Grella, M. A. M. Carai, P. Lazzari, L. Pani, G. A. Pinna, Bioorg. Med. Chem. 13, 3309 (2005); J. M. Mussinu, S. Ruiu, A. C. Mule, A. Pau, M. A. M. Carai, G. Loriga, G. Murineddu, G. A. Pinna, Bioorg. Med. Chem. 11, 251 (2003); Sanofi-Synthelabo WO200132663.; Searle & Co, U.S. Pat. No. 3,940,418, GB1382-773; Pharmacia Corp. WO2003024935; G. A. Pina, M. A. Pirisi, J-M. Mussinu, G. Murineddu, G. Loriga, A. Pau, G. E. Grella, Il Pharmaco 58, 749 (2003)).

Generally, tetralones of type III (see Scheme I) are used as starting materials and condensation of these with oxalate esters under appropriate basic conditions, well known to those of skill in the art, provides ethyl 2-oxo-2-(1-oxo-1,2,3,4-tetrahydronaphthalen-2-yl)acetates of general structure IV (generally existing in their enolate forms, and isolated occasionally as alkalimetal salts). Reaction of IV with substituted aryl hydrazines and heteroaryl hydrazines under appropriate conditions leads to 4,5-dihydro-1H-benzo[g]indazole-3-carboxylic esters (VI). These, upon saponification (VI→VII) and treatment with amines, under well known amidation conditions, leads to the required amides of general structure VIII.

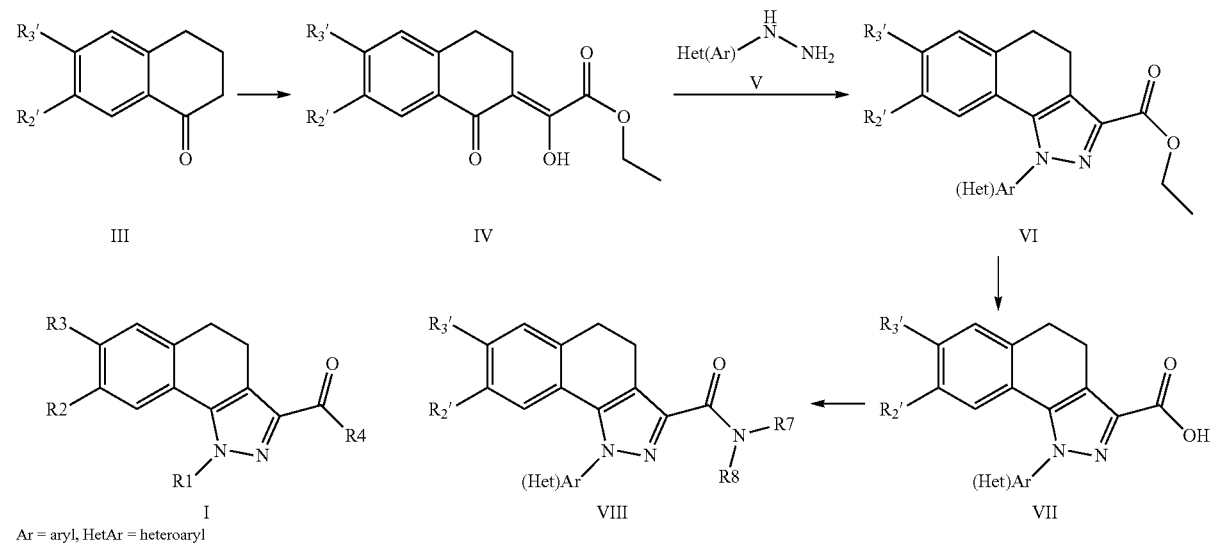

Scheme I

Ar = aryl, HetAr = heteroaryl

The substituents R2-R3 can already be present in the starting material III and may be carried unchanged through the synthesis. In that case R2'-R3' is equal to R2-R3. In order to diversify the substituents R2-R3 on the phenyl moiety of derivatives of general formula I (or VIII) halogen atoms (preferentially bromine and iodine) may serve as masked functionalities (R2'-R3') to be converted in later stages of the synthesis to various target substituents (R2-R3), e.g. via lithiation followed by reaction with electrophilic reagents to generate carboxylates, carboxaldehydes (serving as precursors for olefins via subsequent Wittig reaction, or for amines via reductive amination) or hydroxymethyl groups (and derived ethers and esters).

Alternatively, aryl halogens (R2'-R3') can be employed as reactive substrates in well known organometallic reactions like Ullmann, Suzuki-, Stille-, Sonogashira-, Heck- and Buchwald protocols to create new carbon-carbon single, double and triple bonds, carbon nitrogen bonds (aniline derivatives) and nitriles (A. Suzuki, *Chem. Comm.* 4759 (2005); Bach et al. *Tetrahedron* 61, 2245 (2005); Rossi et al. *Synthesis* 2419 (2004); Muci and Buchwald, Practical Palladium Catalysts for C—N and C—O bond formation, in *Topics in current Chemistry-Cross-coupling Reactions*, Vol. 219, N. Miyaura., Ed., Springer Verlag, Heidelberg, 131-209, (2002); Hartwig, Palladium-catalyzed Amination of Aryl Halides and Related Reactions, in *Handbook of Organopalladium Chemistry for Organic Synthesis*, Vol 1, 1051-1096 (2002), E. Negishi Ed., J. Wiley & Sons: New York; Schlummer et al. *Advanced Synthesis and Catalysis* 346 (13-15), 1599 (2004); *Transition Metals for Organic Synthesis*, M. Beller, C. Bolm Ed., Wiley-VCH Verlag GmbH & Co, Weinheim, Germany). These, in turn, may serve as substrates for further functionalization, like mono- and dihydroxylation (from alkenes), or conversion into triazoles (from acetylenes; "click chemistry") and into tetrazoles (from nitriles).

Demasking phenolic OH groups by e.g. selective cleavage of isopropoxy ethers (in R2'-R3') with electrophilic reagents like $BCl_3$, followed by conversion into reactive sulphonate esters (e.g. triflates) allows for introduction of heterocyclic structures via heteroaryl boronic acids or organotin derivatives, analogous to the above mentioned protocols starting from halogenated aryl groups. Conversion of aryl halogens (in R2'-R3') into boronic acids (either via lithiation or transition metal-mediated boronation), followed by oxidation, provides a means of introducing alternative oxygen functionalities, well known to those skilled in the art. The phenolic functions arising from the deprotected alkoxy ethers (in R2'-R3') can also be used for formation of aryl-aryl and aryl-heteroaryl ethers via Cu-mediated coupling with boronic acids and (hetero)aryl halides. Meaning and application of these reactions is amply explained in some selected literature sources outlined below.

Phenolic triflates (R2'-R3') can be (similarly as described for aryl bromides, vide supra) employed for the introduction of amine and amide functionalities (in R2-R3) by palladium-mediated coupling of either carbamates, carbonamides, imines and silyl amides in processes known as Buchwald-Hartwig amination reactions. Alternatively, nitro groups introduced in an early stage of the synthesis (R2'-R3') enable the preparation of target molecules of general structure I incorporating amine and amide functionalities.

Tetralones (III), used as starting materials are either commercially available or accessible via well known literature procedures. A range of aryl- and heteroaryl hydrazines are commercially available materials and as far as very specific ones are needed, procedures are described in literature which make them available in convenient ways, such as diazotation and subsequent reduction of the diazonium salt (J. Clayden, N. Greeves, S. Warren, P. Wothers in: *Organic Chemistry*, Oxford University Press, Oxford, 2001) with low valent metal salts of inorganic reductant like sulfite, by organolithium mediated substitution with azodicarboxylates followed by decarboxylation (Bayer Pharmaceutical Corporation, WO2007027842), by organometal mediated coupling of Boc-protected hydrazine (L. Jiang, X. Lu, H. Zhang, Y. Jiang, D. Ma, *J. Org. Chem.* 74, 4542 (2009)), by substitution of reactive halogens directly with hydrazine (H. Beyer, S. Melde, *Journal Prakt. Chem.* 24 (1), 91 (1964)), or by electrophilic amination of aromatic and heteroaromatic amines (C. Galves, F. Garcia, *J. Heterocyclic Chem.* 21, 393 (1984); E. Colvin, G. Kirby, A. Wilson, *Tetrahedron Lett.* 23, 3835 (1982); Y. Shen, G. K. Friestad, *J. Org. Chem.* 67, 6236 (2002).

The compounds of the invention may form hydrates or solvates. It is known to those of skill in the art that charged compounds form hydrated species when lyophilized with water, or form solvated species when concentrated in a solution with an appropriate organic solvent. The compounds of this invention include the prodrugs, hydrates or solvates of the compounds listed.

A discussion of prodrugs is provided in T. Higuchi and V. Stella, Pro-drugs as Novel Delivery Systems (1987) 14 of the A.C.S. Symposium Series and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol and the like and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates and the like. "Hydrate" is a solvate wherein the solvent molecule is $H_2O$.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

The compounds of Formula I may contain asymmetric or chiral centers and, therefore, exist in different stereoisomeric forms. It is intended that all stereoisomeric forms of the compounds of Formula I as well as mixtures thereof, including racemic mixtures, form part of the present invention. In addition, the present invention embraces all geometric isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral HPLC column.

It is also possible that the compounds of Formula I may exist in different tautomeric forms and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Certain isotopically-labelled compounds of Formula (I) (e.g., those labeled with $^3$H, $^{14}$C, $^{18}$F and $^{11}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

The dihydrobenzoindazole compounds of the invention were found to stimulate the FSH receptor. Methods to determine receptor binding, as well as in vitro and in vivo assays to determine biological activity, of gonadotropins are well known. In general, expressed receptor is incubated with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell, but other cells are also suitable. Preferably the cells are of mammalian origin (Jia et al, *Mol. Endocrin.*, 5, 759-776, (1991)).

Methods to construct recombinant FSH receptor expressing cell lines are well known in the art (Sambrook et al., Molecular Cloning: a Laboratory Manual, Cold Spring Harbor Laboratory Press, Cold Spring Harbor). Expression of receptor is attained by expression of the DNA encoding the desired protein. Techniques for site directed mutagenesis, ligation of additional sequences, PCR and construction of suitable expression systems are all, by now, well known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then incubated with the test compound to observe binding of the test compound, or stimulation of a functional response.

Alternatively, isolated cell membranes containing the expressed receptor may be used to measure binding of the test compound.

For measurement of binding, radioactive or fluorescent compounds may be used. Such compounds are also part of the invention.

In the alternative also competition binding assays may be performed.

Another assay involves screening for FSH receptor agonistic compounds by determining stimulation of receptor mediated cAMP accumulation. Thus, such a method involves expression of the receptor in a host cell and exposing the cell to the test compound. The amount of cAMP is then measured. The level of cAMP will be increased, by the stimulating effect of the test compound upon binding to the receptor.

For the measurement of intrinsic activity human recombinant FSH can be used as a reference compound.

In addition to direct measurement of e.g. cAMP levels in the exposed cell, cells lines can be used which in addition to transfection of DNA encoding the FSH receptor are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch., Himmler, A. and Czernilofsky, A. P., *Curr. Opin. Biotechnol.*, 6, 574-581 (1995).

The present invention also relates to a pharmaceutical composition comprising a dihydrobenzoindazole derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

Compositions include e.g. those suitable for oral, sublingual, subcutaneous, intravenous, intramuscular, nasal, local, or rectal administration and the like, all in unit dosage forms for administration.

For oral administration, the active ingredient may be presented as discrete units, such as tablets, capsules, powders, granulates, solutions, suspensions and the like.

For parenteral administration, the pharmaceutical composition of the invention may be presented in unit-dose or multi-dose containers, e.g. injection liquids in predetermined amounts, for example in sealed vials and ampoules and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The pharmaceutical composition might also include additional therapeutically active agents, in particular those that are to be used in the same regimen. Such agents include but are not limited to other gonadotropin agonists and GnRH modulators.

The invention thus also includes a pharmaceutical composition, as hereinbefore described which further comprises at least one additional therapeutically active agent.

The exact dose and regimen of administration of the active ingredient, or a pharmaceutical composition thereof, may vary with the particular compound, the route of administration and the age and condition of the individual subject to whom the medicament is to be administered.

In general, parenteral administration requires lower dosages than other methods of administration which are more dependent upon absorption. However, a suitable dosage for humans may be 0.05-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

The compounds according to the invention can be used in therapy. They can be used for the same clinical purposes as the native FSH.

A further aspect of the invention resides in the use of dihydrobenzoindazole compounds having the general formula I for the manufacture of a medicament to be used for the treatment of disorders responsive to FSH receptor mediated pathways, preferably for the treatment of fertility disorders. Thus, patients in need thereof can be administered with suitable amounts of the compounds according to the invention.

In yet another aspect the invention resides in the use of dihydrobenzoindazole compounds having the general formula I for the manufacture of a medicament to be used for the treatment of infertility. In particular the compounds can be used to induce ovulation (OI) or in controlled ovarian stimulation (COS) protocols.

The invention is illustrated by the following examples.

EXAMPLES

General Comments

The following abbreviations are used in the examples: DIPEA=N,N-diisopropylethylamine, HATU=O-(7-azabenzotriazole-1-yl)-N,N,N',N'-tetramethyluronium hexafluorophosphate, DMF=N,N-dimethyl-formamide, DME=1,2-dimethoxyethane, THF=tetrahydrofuran, Boc=t-butoxycarbonyl, NMP=N-methylpyrrolidone, TBTU=O-benzotriazol-1-yl-N,N,N,N'-tetrabutyluronium tetrafluoroborate, hexafluorophosphate, DMAP=4-(dimethylamino) pyridine.

The names of the final products described in the examples were generated using Chem Draw Ultra program. Microwave reactions were carried out on a Biotage (model: Initiator) microwave oven with autosampler.

Thin Layer Chromatography (TLC) was conducted on Merck TLC plates (5×10 cm) silica gel 60 $F_{254}$.

Example 1

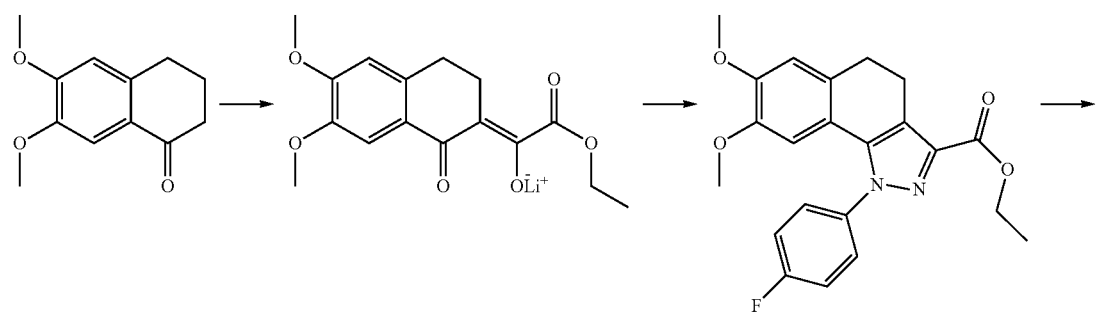

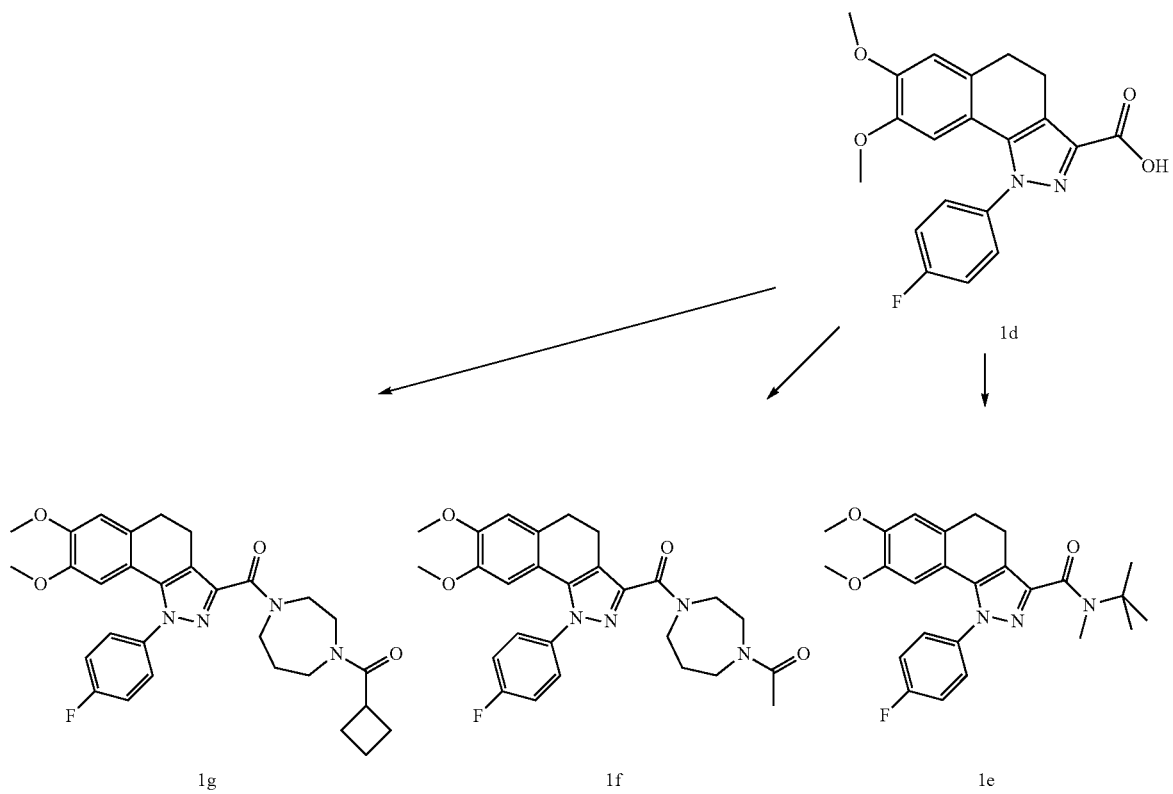

N-tert-butyl-1-(4-fluorophenyl)-7,8-dimethoxy-N-methyl-4,5-dihydro-1H-benzo[g]indazole-3-carboxamide 1e 1-(4-(1-(4-fluorophenyl)-7,8-dimethoxy-4,5-dihydro-1H-benzo[g]indazole-3-carbonyl)-1,4-diazepan-1-yl)ethanone 1f (4-(cyclobutanecarbonyl)-1,4-diazepan-1-yl)(1-(4-fluorophenyl)-7,8-dimethoxy-4,5-dihydro-1H-benzo[g]indazol-3-yl)methanone 1g To a solution of 1.47 g of 6,7-dimethoxytetralone and 1.1 ml of diethyl oxalate in 30 ml of diethyl ether was added dropwise in 5 min, a solution of 0.8 ml of 1M lithium hexamethyl disilazide in THF. The mixture was stirred for an additional 16 hr. The precipitate of lithium salt was filtered and washed with diethyl ether to provide 2.2 g of 1b as a yellow solid, which was used without further purification in the next step. MS-ESI: [M+H]$^+$ 261.22.

A suspension of 517 mg of 1b and 300 mg of 4-fluorophenyl hydrazine.hydrochloride in 13 ml of acetic acid was stirred for several hours at RT and then heated in an oil bath for 16 hr at 80° C. The mixture was cooled to RT and poured into 40 ml of water. The solid which formed, was filtered, washed with water and ethanol and dried in vacuo (50° C.) to provide 480 mg of 1c as a light yellow solid. MS-ESI: [M+H]$^+$ 397.07.

NMR (CDCl$_3$) δ 1.44 (t, 3, CH$_3$), 2.95, 3.07 (2×t, 4, 2×CH$_2$), 342, 3.88 (2×s, 6, 2×OCH$_3$), 4.45 (q, 2, OCH$_2$), 6.25, 6.85 (2×s, 2, 2×Ar—H), 7.21 and 7.54 (2×m, 4, Ar(F)—H).

A suspension of 500 mg of 1c in 20 ml of dioxane was mixed with 4 ml of 4N NaOH. The mixture was stirred at 80° C. for 16 hr and then concentrated to about 10 ml of volume. Then, 20 ml of water was added and the solution was acidified to pH2 by addition of 1N HCl. The product which precipitated was filtered and dried, to give 463 mg of 1d. MS-ESI: [M+H]$^+$ 369.03.

A solution of 98 mg of 1d, 125 mg of HATU, 220 μl of DiPEA and 130 μl of N,2-dimethylpropan-2-amine in 6 ml of dichloromethane was stirred at RT, until completion (tlc). The organic layer was washed with 5% aq. citric acid and water and then dried and concentrated. The crude product was purified by chromatography over silica gel (using a gradient of toluene/ethyl acetate). This gave 102 mg of 1e.

NMR (CDCl$_3$) δ 1.54 (s, 9, tertC$_4$H$_9$), 2.86 and 2.92 (2×m, 4, 2×CH$_2$), 3.11 (s, 3, NCH3), 3.43 and 3.88 (2×s, 6, 2×OCH$_3$), 6.28 and 6.81 (2×s, 2, Ar—H), 7.20 and 7.52 (2×m, 4, Ar(F)H.). MS-ESI: [M+H]$^+$ 438.17.

In a similar way were prepared:

1f: NMR (CDCl$_3$) δ 1.91 and 2.05 (2×m, 2, CH$_2$), 2.18 (s, 3, acetyl) 3.45 and 3.90 (2×s, 6, 2×OCH$_3$), 3.52-4.08 (br.m, 8, 4×CH$_2$), 6.30 and 6.82 (d+bs, 2, Ar—H), 7.22 and 7.53 (2×m, 4, Ar(F)H). MS-ESI: [M+H]$^+$ 493.23.

1g: NMR (CDCl$_3$) δ 1.80-2.45 (br m, 8, 4×CH$_2$), 3.30 (m, 1, CH), 3.40-4.02 (br m, 8, 4×CH$_2$) 3.46 and 3.90 (2×s, 6, 2×OCH$_3$), 6.30 and 6.82 (2× double s, 2, ArH, rotamers), 7.21 and 7.51 (2×m, 4, Ar(F)H). MS-ESI: [M+H]$^+$ 533.28.

Example 2

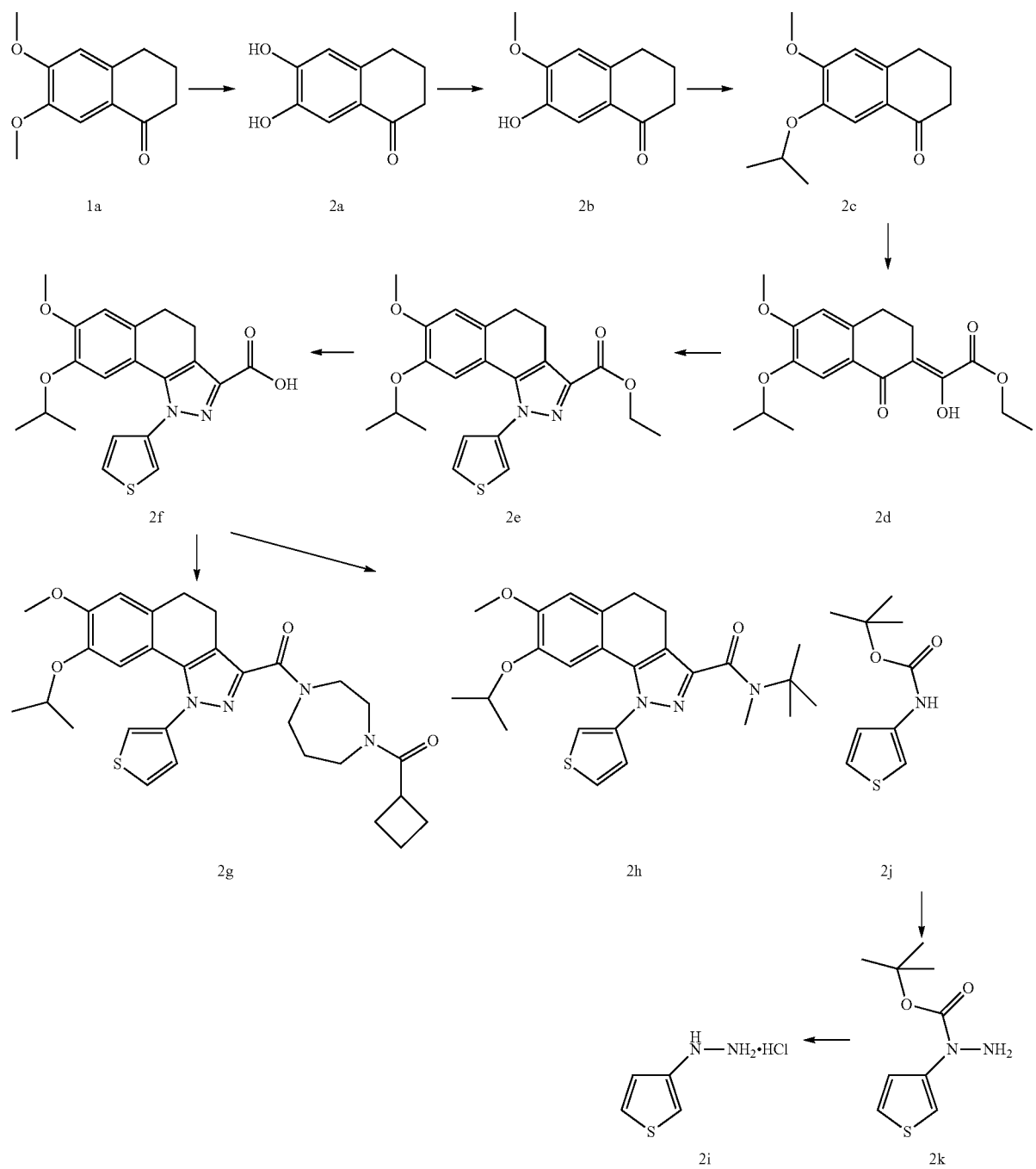

N-tert-butyl-8-isopropoxy-7-methoxy-N-methyl-1-(thiophen-3-yl)-4,5-dihydro-1H-benzo[g]indazole-3-carboxamide 2h
(4-(cyclobutanecarbonyl)-1,4-diazepan-1-yl)(8-isopropoxy-7-methoxy-1-(thiophen-3-yl)-4,5-dihydro-1H-benzo[g]indazol-3-yl)methanone 2g 6-methoxy-7-isopropoxy-1-tetralone was prepared by a modification of a literature prescription (R. Beugelmans, J. Chastanet, H. Ginsbur, L. Quintero-Cortes, G. Roussi, *J. Org. Chem.* 50, 4933 (1985). A suspension of 15 g 6,7-dimethoxytetralone 1a in 200 ml of dichloromethane was treated at −78° C. with 19 ml of boron tribromide. The cooling device was removed and the mixture was stirred for two hours at ambient temperature and then poured into 400 ml of ice-water. Subsequently, 10 ml of 2N HCl and 500 ml of ethyl acetate were added and the mixture was stirred for an additional ½ hr. The organic layer was separated, washed several times with sat. NaCl, dried and concentrated, to provide 12 g of 2a as a pink solid.

NMR (DMSO-d$^6$) δ 1.94 (m, 2, CH$_2$), 2.43 (t, 2, CH$_2$), 2.73 (t, 2, CH$_2$), 6.61 and 7.22 (2×s, 2, Ar—H).

A solution of 11.5 g of 2a and 9 g of $K_2CO_3$ in 100 ml of DMF was stirred for 15 min at RT and then 4 ml of methyl iodide was added. Stirring was continued for 2 hr. The reaction mixture was poured into 600 ml of water and the reaction was acidified by addition of 6N HCl, to pH4. The product was extracted into ethyl acetate. The organic extract was washed several times with water, dried and concentrated. The product was purified by chromatography over silica gel, using a gradient of toluene/ethylacetate as eluent. This provided 6.5 g of 2b; NMR (DMSO-d$^6$) δ 9.23 (s, 1, OH), 7.24 and 6.84 (2×s, 2, Ar—H), 3.83 (s, 3, OCH$_3$), 2.82 (t, 2, CH$_2$), 2.48 (t, 2, CH$_2$), 1.98 (m, 2, CH$_2$).

A mixture of 5.2 g of 2b and 12 g of $K_2CO_3$ in 30 ml of DMF was stirred for 10 min. Then, 5 ml of isopropyl bromide was added and the reaction mixture was stirred for an additional 16 hr at 65° C. The reaction mixture was cooled and poured into 200 ml of water and the product was extracted with ethyl acetate. The extract was washed twice water, dried and concentrated, to provide 6.2 g of 2c. MS-ESI: [M+H]$^+$ 235.16. NMR δ (CDCl$_3$): δ 1.38 (d, 6, isoC$_3$H$_7$), 2.11 (m, 2, CH$_2$), 2.61 (t, 2, CH$_2$), 2.89 (t, 2, CH$_2$), 3.91 (s, 3, OCH$_3$), 4.62 (m, 1, CH), 6.67 and 7.53 (2×s, 2, Ar—H).

A solution of 5.95 g of 2c and 4.27 g of diethyl oxalate in 95 ml of dry diethyl ether (under N$_2$ atmosphere) was treated with 29.2 ml of a 1M solution of lithium bistrimethylsilyl amide in THF. The mixture was stirred for 1 hr and then 50 ml of ethyl acetate was added, followed by 100 ml of 1N HCl. The reaction mixture was stirred for 5 min and the product was extracted into ethyl acetate. The extract was washed twice with water, dried, concentrated and the material thus isolated was purified by chromatography over silica gel, using a gradient of toluene/ethyl acetate as eluent. This gave 7.65 g of 2d. NMR (CDCl$_3$) δ 1.42 (d and t, 9, OCH$_2$CH$_3$ and isoC$_3$H$_7$), 2.83 (m, 2, CH$_2$), 2.97 (t, 2, CH$_2$), 3.92 (s, 3, OCH$_3$), 4.38 (q, 2, OC$_2$H$_5$), 4.63 (m, 1, CH), 6.69 and 7.51 (2×s, 2, Ar—H).

A mixture of 97 mg of 2d, 144 mg of 21.10 mg of pTsOH and 5 ml of abs. ethanol was heated in a microwave reactor for 40 min at 100° C. The reaction mixture was then cooled and diluted with 20 ml of 5% aq. NaHCO$_3$ and extracted with ethyl acetate. The extract was washed with water, dried, concentrated and the residue was purified by chromatography over silica gel, using a gradient of heptane/ethyl acetate as eluent. This provided 40 mg of 2e; R$_f$ (heptane/ethyl acetate 3/2) 0.40. NMR (CDCl$_3$): δ 1.18 (d, 6, isoC$_3$H$_7$), 1.42 (t, 3, CH$_3$), 2.92 and 3.08 (2×m, 4, 2×CH$_2$), 4.02 (m, 1, CH), 4.43 (q, 2, OCH$_2$), 3.87 (s, 3, OCH$_3$), 6.41 and 6.81 (2×s, 2, Ar—H), 7.23, 7.44 and 7.52 (3×m, 3, thiophene-H).

A solution of chloramine in ether was prepared by addition of 2.2 ml of conc. ammonia with efficient stirring to a mixture of 40 ml of diethyl ether and 18 ml of bleach (4% active chlorine) at 0° C. After stirring for 15 min., the ether layer was decanted off and dried over CaCl$_2$, to provide an approximately 0.24M solution of chloramine.

To a suspension of 320 mg of 60% NaH (dispersion in mineral oil) in 5 ml of DMF was added 800 mg of 2j. The mixture was stirred for ½ hr at 55° C. and then cooled to 0° C. To this mixture was added dropwise 20 ml of the above mentioned chloramine solution in diethyl ether. After stirring for an additional ½ hr the reaction was diluted with 30 ml of water and the product was extracted into ethyl acetate. The extract was washed with water, dried and concentrated and the residue was purified by chromatography over silica gel (using a gradient of heptane/ethyl acetate) as eluent, to provide 680 mg of 2k.

A solution of 400 mg of 2k in 5 ml of dry dichloromethane was treated with 2 ml of 4N HCl in dioxane. The reaction mixture was stirred for 1 hr at RT and then concentrated, to provide 290 mg of 2i. R$_f$ (CH$_2$Cl$_2$/methanol 9/1) 0.60 (starting material R$_f$ 0.90). NMR (CDCl$_3$) δ 1.55 (s, 9, tertC$_4$H$_9$), 4.43 (bs, 2, NH$_2$), 7.12, 7.20 and 7.37 (3×m, 3, thiophene-H)

A solution of 85 mg of 2e in 5 ml of dioxane and 2 ml of 2N aq. LiOH were mixed and heated for 5 min in a microwave reactor at 150° C. The mixture was diluted with 20 ml of water, once washed with ether, the aqueous phase was acidified with 1N HCl and the product was extracted with ethyl acetate. The extract was washed twice with water, dried and concentrated, to provide 75 mg of acid 2f. R$_f$ 0.30 (dichloromethane/methanol 9/1).

A mixture of 41 mg of 2f, 30 µl of N-methyl-N-tert-butylamine, 100 µl of DiPEA and 45 mg of TBTU in 2 ml of dichloromethane was stirred for 16 hr at RT. The reaction was poured into 10 ml of 0.5N HCl and the product was extracted with dichloromethane. The organic layer was washed once with water, dried and concentrated. The product was purified by chromatography over silica gel, using a gradient of toluene/ethyl acetate as eluent, to provide 40 mg of 2h. R$_f$ 0.60 (toluene/ethyl acetate 3/2).

MS-ESI: [M+H]$^+$ 454.33

NMR (CDCl$_3$): δ 7.48, 7.41 and 7.20 (3×m, 3,3-thienyl-H), 6.44 and 6.80 (2×s, 2, Ar—H), 4.04 (m, 1, CH), 0.86 (s, 3, OCH$_3$), 3.11 (s, 3, CH$_3$N), 2.92 and 2.87 (2×m, 4, CH$_2$CH$_2$), 1.53 (s, 9, tertC$_4$H$_9$), 1.20 (d, 6, isoC$_3$H$_7$).

A mixture of 48 mg of cyclobutyl(1,4-diazepan-1-yl) methanone, 32 mg of 2f, 100 µl of DiPEA and 45 mg of TBTU in 3 ml of dichloromethane was stirred at RT for 1 hr. The mixture was diluted with 15 ml of 0.5N HCl and extracted with dichloromethane. The organic layer was washed with water, dried, concentrated and the residue was purified by chromatography on reversed phase C18 silica gel, using a gradient of acetonitrile/water as eluent. This provided 44 mg of 2g; R$_f$ 0.50 (CH$_2$Cl$_2$/methanol 9/1). MS-ESI: [M+H]$^+$ 549.31. NMR (CDCl$_3$) δ 7.46 (m, 2, thiophene-H), 7.22 (m, 1, thiophene-H), 6.81 (2×s, 1, Ar—H rotamers), 6.48 (2×s, 1, Ar—H, rotamers), 4.04 (m, 1, isoC$_3$H$_7$), 3.48-4.0 (m, 8, 4×CH$_2$), 3.86 (s, 3, OCH$_3$), 3.29 (m, 1, CH cyclobutyl), 2.52 (m, 4, 2×CH$_2$), 2.36, 2.18, 2.00, 1.86 (4×m, 8, 4×CH$_2$), 1.20 (d, 6, isoC$_3$H$_7$).

Example 3

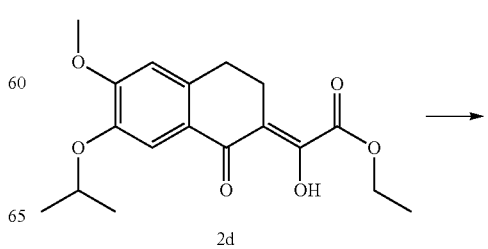

2d

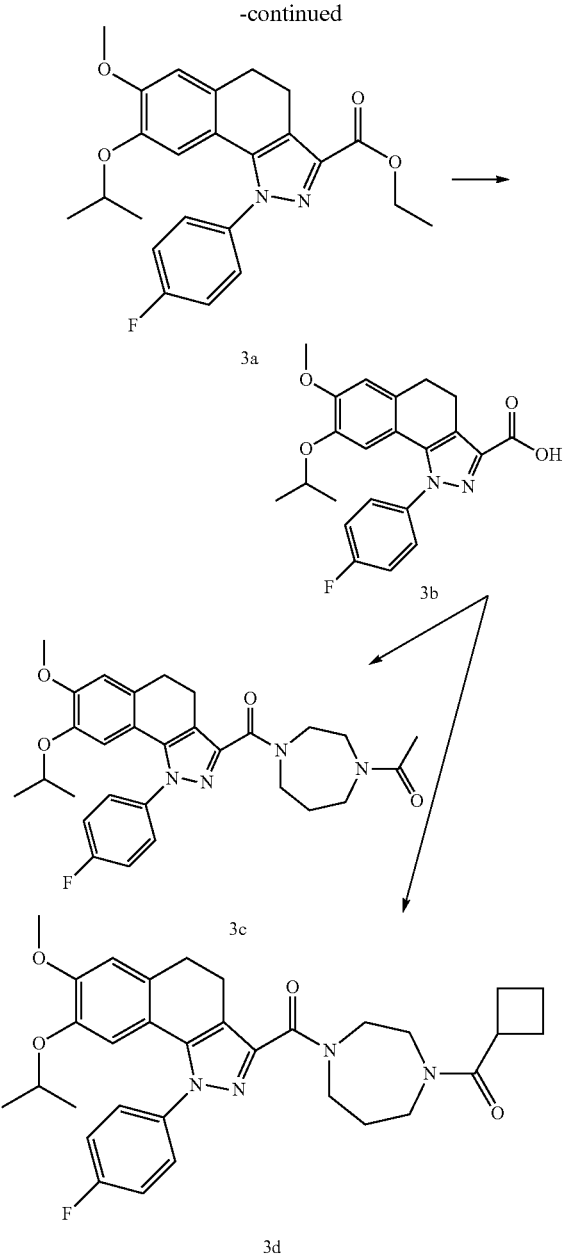

1-(4-(1-(4-fluorophenyl)-8-isopropoxy-7-methoxy-4,5-dihydro-1H-benzo[g]indazole-3-carbonyl)-1,4-diazepan-1-yl)ethanone 3c
(4-(cyclobutanecarbonyl)-1,4-diazepan-1-yl)(1-(4-fluorophenyl)-8-isopropoxy-7-methoxy-4,5-dihydro-1H-benzo[g]indazol-3-yl)methanone 3d A mixture of 120 mg of 2d and 58 mg of 4-fluorophenyl hydrazine hydrochloride in 3 ml of abs. ethanol was heated in a microwave oven at 155° C. for 10 min. The reaction mixture was cooled and the precipitate was filtered, washed with cold ethanol and dried, to provide 95 mg of 3a; Rf (heptane/ethyl acetate 1/1) 0.60 (for 2d Rf 0.65).

NMR (CDCl$_3$): δ 7.53 (m, 2, Ar(F)H), 7.20 (m, 2, Ar(F)H), 6.81 and 6.21 (2×s, 2, Ar—H), 4.06 (q, 2, CH$_2$O), 3.90 (m, 1, CH isoC$_3$H$_7$), 3.88 (s, 3, OCH3), 3.10 and 2.93 (2×t, 4, CH$_2$CH$_2$) 1.43 (t, 3, OCH$_2$CH$_3$), 1.14 (d, 6, isoC$_3$H$_7$).
MS-ESI: [M+H]$^+$ 425.21.

A solution of 95 mg of 3a in 0.5 ml of ethanol and 40 mg of KOH in 0.5 ml of water were mixed and heated at 80° C. for 1 hr. The reaction mixture was cooled, diluted with 3 ml of water and acidified with 0.5N HCl to pH3. The precipitate was filtered, washed with water and cold methanol and dried in vacuo, to give 65 mg of 3b; MS-ESI: [M+H]$^+$ 397.1. NMR (CDCl$_3$) δ 1.12 (d, 6, isoC$_3$H$_7$), 2.93 and 3.09 (2×t, 4, CH$_2$CH$_2$), 3.87 (s, 3, OCH$_3$), 3.93 (m, 1, CH isoC$_3$H$_7$), 7.56 (m, 2, Ar(F)H), 7.23 (m, 2, Ar(F)H), 6.83 and 6.27 (2×s, 2, Ar—H), A mixture of 37 mg of 3b, 47 mg of HATU, 60 μl of DiPEA and 20 mg of 1-(1,4-diazepan-1-yl)ethanone in 0.5 ml of dichloromethane was stirred at RT for 16 hr. The reaction was diluted with 3 ml of 0.5N HCl and extracted with dichloromethane. The organic extract was washed once with 5% aq. NaHCO$_3$, dried and concentrated. The crude material was purified by chromatography over reversed-phase silica gel, using a gradient of acetonitrile/water, to give 23 mg of 3c; MS-ESI: [M+H]$^+$ 521.5. NMR (CDCl$_3$) δ 7.48 (m, 2, Ar(F)H), 7.19 (m, 2, Ar(F)H), 6.81 (2×s, 1, ArH-rotamers, 6.30 (2×s, 1, ArH rotamers), 3.97 (m, 1, CH isoC$_3$H$_7$), 3.86 (s, 3, OCH$_3$), 3.52-4.04 (m, 8, CH$_2$ azepine) 2.90-2.98 (m, 4, CH$_2$CH$_2$), 2.14 (2×s, 3, CH$_3$ rotamers) 1.87 and 2.03 (2×m, 2, CH$_2$ azepine), 1.16 (d, 6, isoC$_3$H$_7$).

In a similar way as described for 3c, from 37 mg of 3b and 20 mg of cyclobutyl(1,4-diazepan-1-yl)methanone was prepared 42 mg of 3d; MS-ESI: [M+H]$^+$ 561.5. NMR (CDCl$_3$) δ 7.48 (m, 2, Ar(F)H), 7.20 (m, 2, Ar(F)H), 6.81 (2×s, 1, ArH-rotamers, 6.30 (2×s, 1, ArH rotamers), 3.96 (m, 1, CH isoC$_3$H$_7$), 3.85 (s, 3, OCH$_3$), 3.45-4.00 (m, 8, CH$_2$ azepine), 3.29 (m, 1, cyclobutyl-H), 2.86-3.00 (m, 4, CH$_2$CH$_2$), 2.14 (2×s, 3, CH$_3$ rotamers) 1.80-2.40 (m, 6, CH$_2$ cyclobutyl)), 1.16 (d, 6, isoC$_3$H$_7$).

Example 4

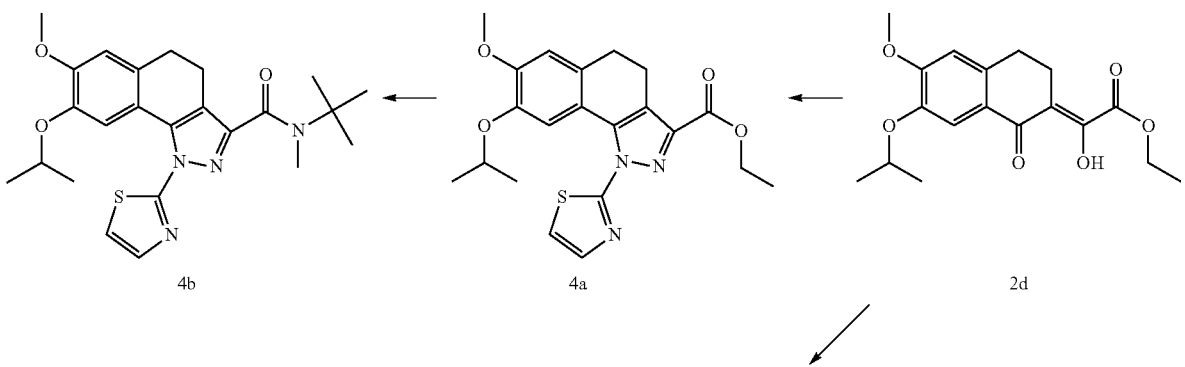

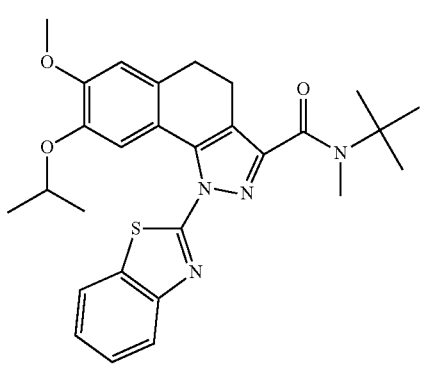

4d

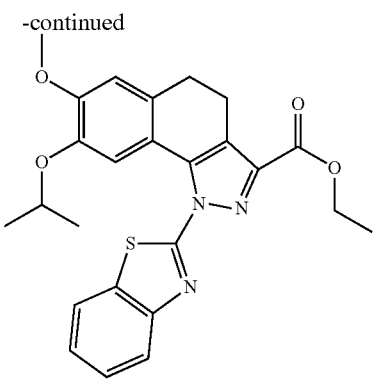

4c 1-(benzo[d]thiazol-2-yl)-N-tert-butyl-8-isopropoxy-7-methoxy-N-methyl-4,5-dihydro-1H-benzo[g]indazole-3-carboxamide 4d 1-(thiazol-2-yl)-N-tert-butyl-8-isopropoxy-7-methoxy-N-methyl-4,5-dihydro-1H-benzo[g]indazole-3-carboxamide 4b A solution of 125 mg of 2d and 48 mg of 2-hydrazino-1,3-thiazole in 3 ml of acetic acid was heated at 100° C. for 16 hr. The mixture was poured into water and neutralized by addition of sufficient solid NaHCO$_3$. The product was extracted with ethyl acetate and the extract was dried and concentrated, followed by chromatography over silica gel (using a gradient of heptane/ethyl acetate as eluent). This provided 90 mg of 4a as an off-white solid.

NMR (CDCl$_3$) δ 1.33 (d, 6, isoC$_3$H$_7$), 1.43 (t, 3, CH$_3$), 2.91 and 3.03 (2×t, 4, CH$_2$CH$_2$), 3.88 (s, 3, OCH$_3$) 4.32 (m, 1, CH), 4.46 (q, 2, CH$_2$) 6.89 and 7.40 (2×s, 2, Ar—H), 7.38 and 7.67 (2×d, 2, thiazole-H). MS-ESI: [M+H]$^+$ 414.16.

A mixture of 84 mg of 4a and 0.8 ml of 2N aq. NaOH in 4 ml of ethanol was heated at 60° C. for 1 hr. The reaction mixture was cooled, 5 ml of water was added and the reaction mixture was acidified to pH3 with 0.5N HCl. The precipitate was filtered and dried, to give 83 mg of the carboxylic acid. MS-ESI: [M+H]$^+$ 414.16. NMR (DMSO-d$^6$) δ 1.21 (d, 6, isoC$_3$H$_7$), 2.88 (m, 4, CH$_2$CH$_2$), 3.80 (s, 3, OCH$_3$), 4.23 (m, 1, CH), 7.12 and 7.18 (2×s, 2, Ar—H), 7.80 and 7.88 (2×d, 2, thiazole-H).

A mixture consisting of 75 mg of the above mentioned carboxylic acid, 160 μl of DiPEA, 92 mg of TBTU, 0.2 ml of DMF and 2 ml of dichloromethane was stirred for ½ hr at RT. Then, 30 μl of N-methyl-tert-butylamine was added and stirring was prolonged for 16 hr. To the mixture was added 10 ml of water and the product was extracted with dichloromethane. The organic layer was dried and concentrated and the product was chromatographed over silica gel, using a gradient of heptane/ethyl acetate as eluent, to provide 69 mg of 4b; MS-ESI: [M+H]$^+$ 455.3. NMR (DMSO d$^6$) δ 1.23, (d, 6, isoC$_3$H$_7$), 1.47 (s, 9, tertC$_4$H$_9$), 2.64 and 2.85 (2×m, 4, CH$_2$CH$_2$), 3.33 (s, 3, NCH$_3$), 3.80 (s, 3, OCH$_3$), 4.10 (m, 1, CH), 7.12 and 7.61 (2×s, 2, Ar—H), 7.73 and 7.78 (2×d, 2, thiazoleH).

A solution of 103 mg of 2d and 58 mg of 2-hydrazino-benzothiazole in 2 ml of acetic acid was heated at 100° C. for 16 hr. The mixture was poured into water and neutralized by addition of sufficient solid NaHCO$_3$. The product was extracted with methylene dichloride and the extract was dried and concentrated, followed by chromatography over silica gel (using a gradient of toluene/ethyl acetate as eluent). This provided 123 mg of 4c as an off-white solid; MS-ESI: [M+H]$^+$ 464.11. NMR (CDCl$_3$) δ 1.32 (d, 6, isoC$_3$H$_7$), 1.47 (t, 3, CH$_3$), 2.93 and 3.02 (2×m, 4, CH$_2$CH$_2$), 3.91 (s, 3, OCH$_3$), 4.44 (m, 1, CH), 4.47 (q, 2, OCH$_2$—), 6.85 (s, 1, Ar—H) 7.89 (s, 1, Ar—H) 7.42-7.55 and 7.90 (2×m, 4, thiazole-H).

A mixture of 116 mg of 4c and 1 ml of 2N aq. NaOH in 4 ml of ethanol was heated at 60° C. for 1 hr. The reaction mixture was cooled, 5 ml of water was added and the reaction mixture was acidified to pH3 with 0.5N HCl. The precipitate was filtered and dried, to give 89 mg of the carboxylic acid. NMR (DMSO-d$^6$) δ 1.22 (d, 6, isoC$_3$H$_7$), 2.90 (m, 4, 2×CH$_2$CH$_2$), 3.83 (s, 3, OCH$_3$), 4.41 (m, 1, CH), 7.04 and 7.94 (2×m, 2, Ar—H) 7.50, 7.58, 7.83 and 8.17 (4×m, 4, thiazole-H).

A mixture consisting of 86 mg of the above mentioned carboxylic acid, 165 μl of DiPEA, 95 mg of TBTU, 0.2 ml of DMF and 2 ml of dichloromethane was stirred for ½ hr at RT. Then, 30 μl of N-methyl-N-tert-butylamine was added and stirring was prolonged for 16 hr. To the mixture was added 10 ml of water and the product was extracted with dichloromethane. The organic layer was dried and concentrated and the product was chromatographed over silica gel, using a gradient of heptane/ethyl acetate as eluent, to provide 52 mg of 4d; MS-ESI: [M+H]$^+$ 505.21. NMR (DMSO d$^6$) δ 1.27 (d, 6, isoC$_3$H$_7$), 1.48 (s, 9, tertC$_4$H$_9$), 2.63 and 2.89 (2×m, 4, CH$_2$CH$_2$), 3.0 (s, 3, CH$_3$), 3.82 (s, 3, OCH$_3$), 4.47 (m, 1, CH), 7.07 and 8.12 (2×s, 2, Ar—H), 7.48, 7.56, 7.82 and 7.8.13 (4×m, 4, thiazole-H).

Example 5

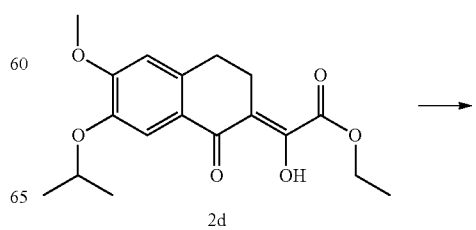

2d

-continued

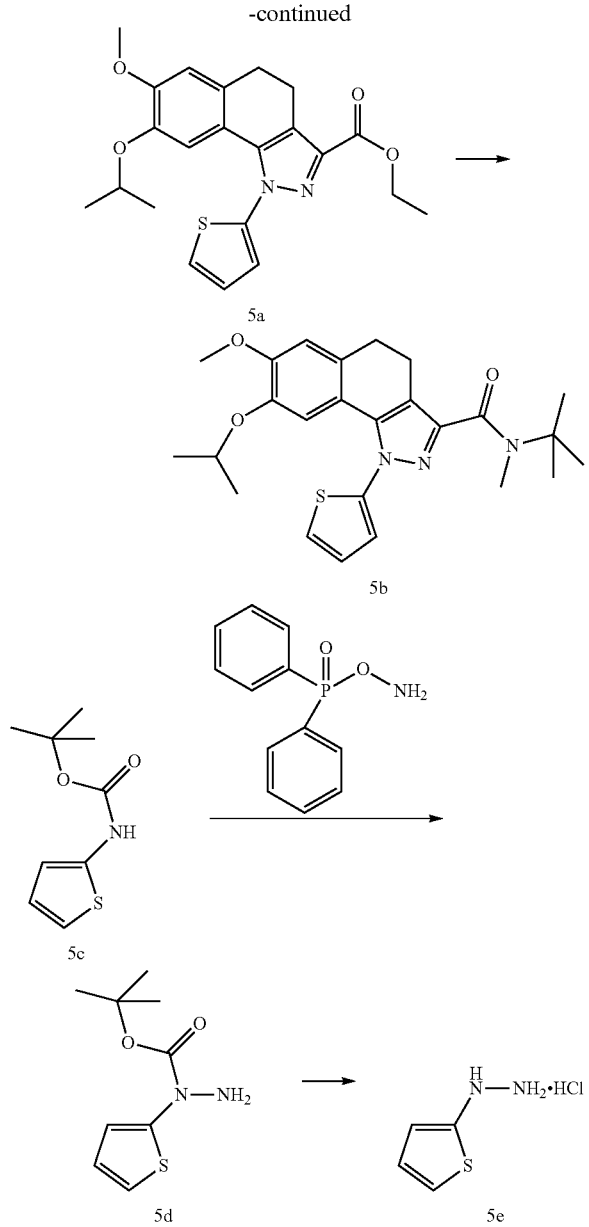

N-tert-butyl-8-isopropoxy-7-methoxy-N-methyl-1-(thiophen-2-yl)-4,5-dihydro-1H-benzo[g]indazole-3-carboxamide 5b A quantity of O-(diphenylphosphoryl)hydroxylamine was prepared according to a literature prescription: E. Colvin, G. Kirby, A. Wilsom, *Tetrahedron Lett.* 23 (37), 3835, (1982); D. Binder, G. Habison, C. Noe, *Synthesis* 487 (1977).

To a suspension of 360 mg of 60% NaH (dispersion in mineral oil) in 12 ml of DMF was added 1.2 g of tent-butyl N-(2-thienyl)carbamate (5c). The mixture was heated for ½ h at 60° C. After cooling to RT, a solution of 2.07 g of O-(diphenylphosphoryl)hydroxylamine in 10 ml of dry DMF was added and stirring was prolonged for 16 hr. The reaction mixture was poured into water, extracted with ethyl acetate and the organic extract was washed with water, dried and concentrated. The residue was purified by chromatography over silica gel, using a gradient of heptane/ethyl acetate as eluent, to provide 1.22 g of 5.; MS-ESI: [M+H]$^+$ 215.20. NMR (CDCl$_3$) δ 1.58 (s, 9, tertC$_4$H$_9$) 4.60 (br·s, 2, NH$_2$), 6.83 (m, 2, thienyl-H), 6.90 (bm, 1, thienyl-H).

To a solution of 208 mg of 5d in 3 ml of methylene chloride was added 3 ml of a 4M HCl solution in dioxane. The reaction mixture was concentrated to dryness and the residue, 147 mg of 5e, was used without further purification in the next step.

A mixture of 145 mg of 5e and 290 mg of 2d in 8 ml of abs. ethanol was stirred at RT overnight. The reaction mixture was concentrated to a small volume and diluted with 10 ml of water. The product was extracted into dichloromethane. The organic extract was dried and concentrated and the residual material was purified by chromatography over silica gel, using a gradient of heptane/ethyl acetate as eluent. The purified material was triturated with diethyl ether to provide 210 mg of 5a; Mp 145° C.; MS-ESI: [M+H]$^+$ 413.17. NMR (CDCl$_3$) δ 1.19 (d, 6, isoC$_3$H$_7$), 1.42 (t, 3, CH$_3$), 2.92 and 3.07 (2×m, 4, 2×CH$_2$), 4.00 (m, 1, CH), 4.43 (q, 2, OCH$_2$), 3.86 (s, 3, OCH$_3$), 6.42 and 6.80 (2×s, 2, Ar—H), 7.08, 7.12 and 7.38 (3×m, 3, thiophene-H).

To a solution of 65 mg of N-methyl-N-tert-butylamine in 1.5 ml of dry THF was added 370 µl of a 2M solution of ethyl magnesium chloride in THF. The mixture was heated at 75° C. for ¾ hr. Then, a solution of 100 mg of 5a in 1 ml of dry THF was added and heating at 75° C. was continued for an additional 1 hr. The reaction mixture was cooled and poured into 5 ml of 5% aq. NH$_4$Cl solution and the product was extracted with ethyl acetate. The extract was dried, concentrated and the crude product was purified by chromatography over silica gel, using a gradient of toluene/ethyl acetate as eluent, to provide 15 mg of 5b. MS-ESI: [M+H]$^+$ 454.4. NMR (DMSO-d$^6$) δ 1.07 (d, 6, isoC$_3$H$_7$), 1.47 (s, 9, tertC$_4$H$_9$), 2.68 and 2.88 (2×m, 4, CH$_2$CH$_2$), 3.00 (s, 3, NCH$_3$), 3.75 (s, 3, OCH$_3$), 3.95 (m, 1, CH), 6.36 and 7.00 (2×s, 2, Ar—H), 7.17, 7.36 and 7.73 (3×m, 3, thiophene-H).

Example 6

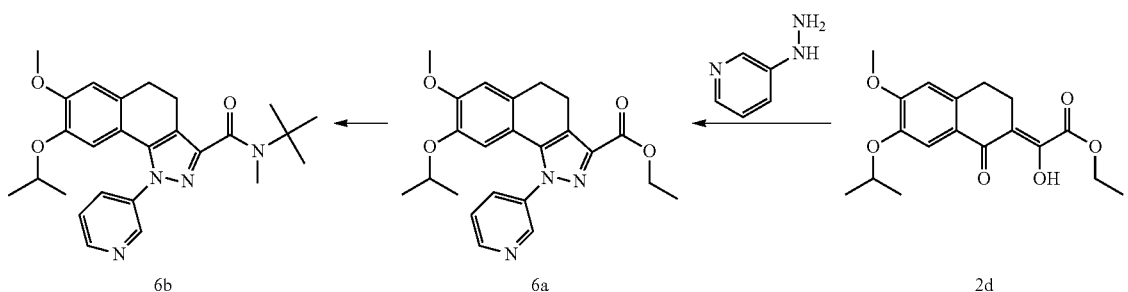

N-tert-butyl-8-isopropoxy-7-methoxy-N-methyl-1-(pyridin-3-yl)-4,5-dihydro-1H-benzo[g]indazole-3-carboxamide 6b A mixture of 104 mg of 2d and 66 mg of 3-hydrazinyl pyridine.dihydrochloride in 2.5 ml of acetic acid was heated at 100° C. for 3 h. The mixture was poured into water and neutralized by addition of portions of solid NaHCO₃. The product was extracted into ethyl acetate. The extract was washed with water, dried and concentrated and the residue was purified by chromatography over silica gel, using a gradient of toluene/ethyl acetate as eluent and provided 110 mg of 6a; MS-ESI: [M+H]⁺ 408.15.

NaHCO₃ and extracted with dichloromethane and the extract was dried and concentrated. The residue was purified by chromatography over silica gel, using a gradient of toluene/acetone as eluent and provided 32 mg of 6b; MS-ESI: [M+H]⁺ 449.3. NMR (DMSO-d⁶) δ 1.00 (d, 6, isoC₃H₇), 1.45 (s, 9, tertC₄H₉), 2.70 and 2.89 (2×m, 4, CH₂CH₂), 3.02 (s, 3, NCH₃), 3.78 (s, 3, OCH₃), 3.87 (m, 1, CH), 6.17 and 7.03 (2×s, 2, Ar—H), 7.63, 8.03 and 8.76 (3×m, 4, pyridine-H).

Example 7

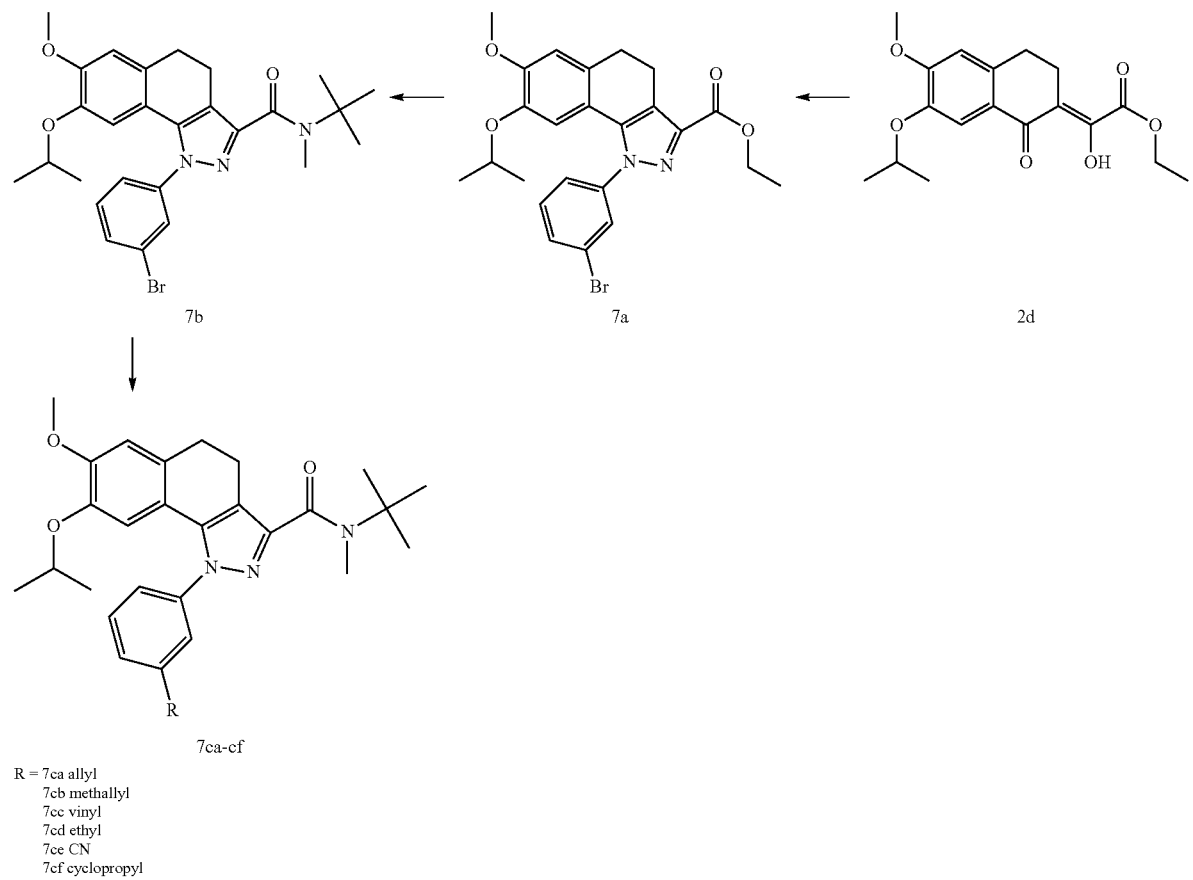

R = 7ca allyl
7cb methallyl
7cc vinyl
7cd ethyl
7ce CN
7cf cyclopropyl

NMR (CDCl₃) δ 1.12 (d, 6, isoC₃H₇), 1.43 (t, 3, CH₃), 2.97 and 3.08 (2×t, 4, CH₂CH₂), 3.87 (s, 3, OCH₃), 3.93 (m, 1, CH), 4.47 (q, 2, CH₂) 6.24 and 6.84 (2×s, 2, Ar—H), 7.48 7.92, 8.74 and 8.85 (4×m, 4, pyridine-H).

A solution of 108 mg of 6a in 4 ml of ethanol was mixed with a solution of 75 mg of lithium hydroxide in 1 ml of water and the mixture was heated at 60° C. for 2 h. The reaction mixture was cooled, diluted with water and sat. aq. ammonium chloride. The product was extracted into dichloromethane. The extract was dried and concentrated, to provide 56 mg of carboxylic acid. MS-ESI: [M+H]⁺ 380.12. NMR (DMSO-d⁶) δ 1.10 (d, 6, isoC₃H₇), 2.90 (m, 4, CH₂CH₂), 3.78 (s, 3, OCH₃), 3.87 (m, 1, CH), 6.11 and 7.02 (2×s, 2, Ar—H), 7.64, 8.12 and 8.74 (3×m, 4, pyridine-H).

A mixture of 51 mg of the carboxylic acid, 110 μl of DiPEA, 66 mg of TBTU, 20 μl of N-methyl-N-tert-butyl-amine in 2 ml of dichloromethane and 0.2 ml of DMF was stirred at RT for 16 hr. The reaction was poured into 5% aq.

N-tert-butyl-1-(3-cyclopropylphenyl)-8-isopropoxy-7-methoxy-N-methyl-4,5-dihydro-1H-benzo[g]indazole-3-carboxamide 7cf
N-tert-butyl-1-(3-cyanophenyl)-8-isopropoxy-7-methoxy-N-methyl-4,5-dihydro-1H-benzo[g]indazole-3-carboxamide 7ce
N-tert-butyl-1-(3-ethylphenyl)-8-isopropoxy-7-methoxy-N-methyl-4,5-dihydro-1H-benzo[g]indazole-3-carboxamide 7cd
N-tert-butyl-8-isopropoxy-7-methoxy-N-methyl-1-(3-vinylphenyl)-4,5-dihydro-1H-benzo[g]indazole-3-carboxamide 7cc
N-tert-butyl-8-isopropoxy-7-methoxy-N-methyl-1-(3-(prop-1-en-2-yl)phenyl)-4,5-dihydro-1H-benzo[g]indazole-3-carboxamide 7cb
1-(3-allylphenyl)-N-tert-butyl-8-isopropoxy-7-methoxy-N-methyl-4,5-dihydro-1H-benzo[g]indazole-3-carboxamide 7ca Compound 7a was prepared from 2d and 3-bromophenyl hydrazine in acetic acid as described for 4a. The product was purified by chromatography; NMR (CDCl$_3$) δ 1.14 (d, 6, isoC$_3$H$_7$), 1.42 (t, 3, CH$_3$), 2.84 and 3.05 (2×t, 4, CH$_2$CH$_2$), 3.88 (s, 3, OCH$_3$), 3.96 (m, 1, CH), 4.45 (q, 2, CH$_2$) 6.33 and 6.83 (2×s, 2, Ar—H), 7.38, 7.50, 7.62 and 7.74 (4×m, 4, BrPhe-H).

Compound 7a was saponified to the carboxylic acid, by heating with NaOH in aqueous ethanol according the method described in example for 4b; NMR (DMSO-d$^6$) δ 1.03 (d, 6, isoC$_3$H$_7$), 2.90 (m, 4, 2×CH$_2$CH$_2$), 3.77 (s, 3, OCH$_3$), 3.90 (m, 1, CH), 6.18 and 7.03 (2×m, 2, Ar—H) 7.60, 7.80, (2×m, 4, BrPhe-H). The carboxylic acid was converted into the amide by reaction with N-methyl-N-tert-butyl-amine according to the method described for 4d, to provide 7b; MS-ESI: [M+H]$^+$ 526.3 and 528.3. NMR (DMSO-d$^6$) δ 1.03 (d, 6, isoC$_3$H$_7$), 1.45 (s, 9, tertC$_4$H$_9$), 2.69 and 2.88 (2×m, 4, CH$_2$CH$_2$), 3.01 (s, 3, NCH$_3$), 3.78 (s, 3, OCH$_3$), 3.93 (m, 1, CH), 6.23 and 7.03 (2×s, 2, Ar—H), 7.57 and 7.78 (2×m, 4, BrPheH).

A mixture of 25 mg of 7b, 13 mg of K$_2$CO$_3$, 15 mg of 2-allyl-4,4,5,5-tetramethyl-1,3,2-dioxaborolane and 5 mg of tetrakis(triphenylphosphine) palladium in 2 ml of degassed 90% aq. dimethoxyethane was heated in a sealed vessel under N$_2$ atmosphere for 16 hr at 90° C. The reaction mixture was cooled and poured into 10 ml of 5% aq. NaHCO$_3$ solution and extracted with dichloromethane. The extract was dried, concentrated and chromatographed over silica gel, using a gradient of heptane/ethyl acetate as eluent, to provide 3 mg of 7ca;

NMR (CDCl$_3$) δ 1.10 (d, 6, isoC$_3$H$_7$), 1.56 (s, 9, tertC$_4$H$_9$), 2.87 and 2.93 (2×m, 4, CH$_2$CH$_2$), 3.13 (s, 3, NCH$_3$), 3.43 (d, 2, CH$_2$) 3.85 (s, 3, OCH$_3$), 3.88 (m, 1, CH), 5.10 (m, 2, allyl), 5.93 (m, 1, allyl), 6.28 and 6.80 (2×s, 2, Ar—H), 7.267-7.43 (m, 4, phenyl-H).

A mixture of 28 mg of 7b, 13 mg of K$_2$CO$_3$, 14 mg of 4,4,5,5-tetramethyl-2-(2-methallyl)-1,3,2-dioxaborolane and 5 mg of tetrakis(triphenylphosphine) palladium in 2 ml of degassed 90% aq. dimethoxyethane was heated in a sealed vessel under N$_2$ atmosphere for 16 hr at 90° C. as described for 7ca to give 21 mg of 7cb. NMR (CDCl$_3$) δ 1.09 (d, 6, isoC$_3$H$_7$), 1.56 (s, 9, tertC$_4$H$_9$), 2.87 and 2.93 (2×m, 4, CH$_2$CH$_2$), 3.13 (s, 3, NCH$_3$), 3.85 (s, 3, OCH$_3$), 3.86 (m, 1, CH), 5.12 (m, 1, methallyl), 5.37 (m, 1, methallyl), 6.32 and 6.80 (2×s, 2, Ar—H), 7.38-7.58 (m, 4, phenyl-H).

A mixture of 56 mg of 7b, 25 mg of K$_2$CO$_3$, 25 mg of 4,4,5,5-tetramethyl-2-(2-vinyl)-1,3,2-dioxaborolane and 10 mg of tetrakis(triphenylphosphine) palladium in 3 ml of degassed 90% aq. dimethoxyethane was heated in a sealed vessel under N$_2$ atmosphere for 16 hr at 90° C. as described for 7ca to give 33 mg of 7 cc. NMR (CDCl$_3$) δ 1.09 (d, 6, isoC$_3$H$_7$), 1.56 (s, 9, tertC$_4$H$_9$), 2.88 and 2.93 (2×m, 4, CH$_2$CH$_2$), 3.14 (s, 3, NCH$_3$), 3.85 (s, 3, OCH$_3$), 3.88 (m, 1, CH), 5.31 (d, 1, vinyl), 5.78 (d, 1, vinyl), 5.71 (dd, 1, vinyl), 6.36 and 6.80 (2×s, 2, Ar—H), 7.38-7.58 (m, 4, phenyl-H).

A solution of 16 mg of 7 cc in 2 ml of abs. ethanol was hydrogenated over 10% Pd/C at 10 bar in an H-Cube reactor (Thales Nanotechnology). After completion of the reaction the mixture was concentrated, to provide 15 mg of 7cd; MS-ESI: [M+H]$^+$ 476.17.

NMR (DMSO-d$^6$) δ 0.98 (dd, 6, isoC$_3$H$_7$), 1.19 (t, 3, CH$_3$), 1.45 (s, 9, tertC$_4$H$_9$), 2.66 (q, 2, CH$_2$), 2.68 and 2.87 (2×m, 4, CH$_2$CH$_2$), 3.02 (s, 3, NCH$_3$), 3.75 (s, 3, OCH$_3$), 3.80 (m, 1, CH), 6.17 and 6.98 (2×s, 2, AR-H), 7.32, 7.41 and 7.49 (3×m, 4, Phe).

A degassed mixture of 40 mg of 7b, 53 mg of zinc cyanide and 8 mg of tetrakis(triphenylphosphine) palladium in 0.8 ml of DMF was heated under N$_2$ atmosphere in a microwave oven for 45 min at 150° C. The reaction mixture was filtered over Celite and the filtrate was diluted with water and extracted with ethyl acetate. The extract was washed with water, dried, concentrated and the residue was chromatographed over silica gel, using a gradient of toluene/ethyl acetate as eluent, to provide 24 mg of 7ce; NMR (DMSO-d$^6$) δ 1.03 (d, 6, isoC$_3$H$_7$), 1.46 (s, 9, tertC$_4$H$_9$), 2.69 and 2.89 (2×m, 4, CH$_2$CH$_2$), 3.02 (s, 3, NCH$_3$), 3.78 (s, 3, OCH$_3$), 3.92 (m, 1, CH), 6.18 and 7.04 (2×s, 2, Ar—H), 7.78, 7.9, 8.03 and 8.12 (4×m, 4, CNPhe-H).

A mixture of 28 mg of 7b, 11 mg of potassium cyclopropyl trifluoroborate, 60 mg of K$_3$PO$_4$ and 6 mg of tetrakis(triphenylphosphine) palladium and 1.5 ml of toluene and 0.5 ml of water was heated under N$_2$ atmosphere for 16 hr. The reaction mixture was cooled, diluted with 5% aq. NaHCO$_3$ and the product was extracted into ethyl acetate. The extract was washed with water, dried and concentrated and the residue was purified by chromatography over silica gel, using a gradient of heptane/ethyl acetate as eluent. This provided 8 mg of 7cf; MS-ESI: [M+H]$^+$ 488.4. NMR (DMSO-d$^6$) δ 0.70 and 0.98 (2×m, 4, cycloC$_3$H$_5$), 1.00 (d, 6, isoC$_3$H$_7$), 1.45 (s, 9, tertC$_4$H$_9$), 2.00 (m, 1, cycloC$_3$H$_5$), 2.70 and 2.88 (m, 4, CH$_2$CH$_2$), 3.02 (s, 3, NCH$_3$), 3.76 (3, 3, OCH$_3$), 3.82 (m, 1, CH), 6.18 and 6.99 (2×s, 2, Ar—H), 7.24 and 7.46 (2×m, 4, Phe).

Example 8

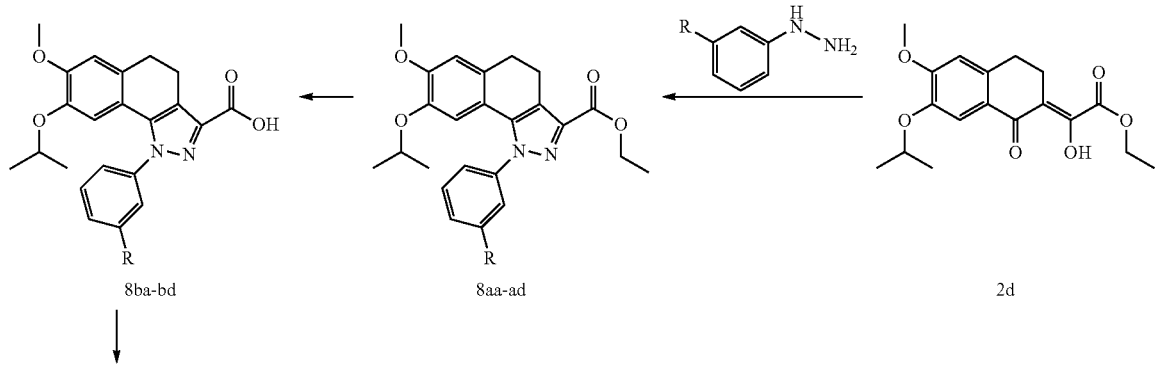

8ba-bd     8aa-ad     2d

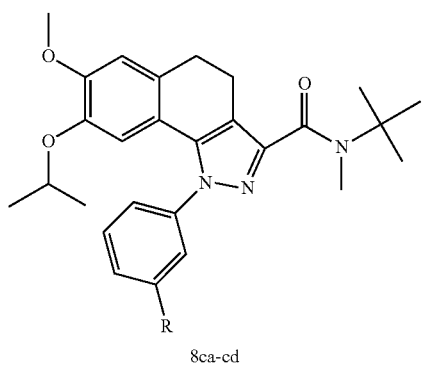

8ca-cd

R = 8ca nitro
   8cb fluoro
   8cc mehoxy
   8cd methyl

N-tert-butyl-8-isopropoxy-7-methoxy-N-methyl-1-m-tolyl-4,5-dihydro-1H-benzo[g]indazole-3-carboxamide 8cd
N-tert-butyl-8-isopropoxy-7-methoxy-1-(3-methoxyphenyl)-N-methyl-4,5-dihydro-1H-benzo[g]indazole-3-carboxamide 8 cc
N-tert-butyl-1-(3-fluorophenyl)-8-isopropoxy-7-methoxy-N-methyl-4,5-dihydro-1H-benzo[g]indazole-3-carboxamide 8cb
N-tert-butyl-8-isopropoxy-7-methoxy-N-methyl-1-(3-nitrophenyl)-4,5-dihydro-1H-benzo[g]indazole-3-carboxamide 8ca According to the method described for 4a, from 124 mg of 2d and 77 mg of 3-nitrophenyl hydrazine hydrochloride, 75 mg of 8aa was obtained. NMR (CDCl$_3$) δ 1.09 (d, 6, isoC$_3$H$_7$), 1.43 (t, 3, CH$_3$) 2.97 and 3.07 (2×m, 4, CH$_2$CH$_2$), 3.87 (s, 3, OCH$_3$), 3.92 (m, 1, CH), 4.47 (q, 2, CH$_2$) 6.28 and 6.87 (2×s, 2, Ar—H), 7.70, 7.94, 8.33 and 8.47 (4×m, 4, NO$_2$Phe-H).

According to the method described for 4a, from 124 mg of 2d and 77 mg of 3-fluorophenyl hydrazine hydrochloride, 66 mg of 8ab was obtained. NMR (CDCl$_3$) δ 1.15 (d, 6, isoC$_3$H$_7$), 1.43 (t, 3, CH$_3$) 2.93 and 3.06 (2×m, 4, CH$_2$CH$_2$), 3.88 (s, 3, OCH$_3$), 3.93 (m, 1, CH), 4.44 (q, 2, CH$_2$) 6.32 and 6.82 (2×s, 2, Ar—H), 7.20, 7.33 and 7.47 (3×m, 4, FPhe-H).

According to the method described for 4a, from 119 mg of 2d and 69 mg of 3-methoxyphenyl hydrazine hydrochloride, 108 mg of 8ac was obtained. NMR (CDCl$_3$) δ 1.12 (d, 6, isoC$_3$H$_7$), 1.42 (t, 3, CH$_3$) 2.94 and 3.08 (2×m, 4, CH$_2$CH$_2$), 3.82 (s, 3, OCH$_3$), 3.86 (s, 3, OCH$_3$), 3.90 (m, 1, CH), 4.45 (q, 2, CH$_2$) 6.32 and 6.80 (2×s, 2, Ar—H), 7.03, 7.08 and 7.38 (3×m, 4, methoxy-Phe-H).

According to the method described for 4a, from 119 mg of 2d and 62 mg of 3-methylphenyl hydrazine hydrochloride, 129 mg of 8ad was obtained. NMR (CDCl$_3$) δ 1.10 (d, 6, isoC$_3$H$_7$), 1.42 (t, 3, CH$_3$), 2.39 (s, 3, CH$_3$), 2.94 and 3.08 (2×m, 4, CH$_2$CH$_2$), 3.86 (s, 3, OCH$_3$), 3.88 (m, 1, CH), 4.43 (q, 2, CH$_2$) 6.31 and 6.80 (2×s, 2, Ar—H), 7.30 and 7.36 (2×m, 4, methyl-Phe-H).

According to the method described for 4b, saponification of 70 mg of 8aa with NaOH provided 53 mg of the carboxylic acid 8ba, which was reacted with N-methyl-N-tert-butylamine to provide 35 mg of 8ca. MS-ESI: [M+H]$^+$ 493.4.

8ba: NMR (DMSO-d$^6$) δ 0.97 (d, 6, isoC$_3$H$_7$), 2.92 (m, 4, CH$_2$CH$_2$), 3.78 (s, 3, OCH$_3$), 3.90 (m, 1, CH), 6.20 and 7.08 (2×m, 2, Ar—H) 7.88, 8.08, 8.38 and 8.42 (4×m, 4, NO$_2$Phe-H).

8ca: NMR (DMSO-d$^6$) δ 0.98 (d, 6, isoC$_3$H$_7$), 1.47 (s, 9, tertC$_4$H$_9$), 2.70 and 2.91 (2×m, 4, CH$_2$CH$_2$), 3.01 (s, 3, NCH$_3$), 3.79 (s, 3, OCH$_3$), 3.92 (m, 1, CH), 6.25 and 7.07 (2×s, 2, Ar—H), 7.96, 8.05, 8.33 and 8.38 (4×m, 4, NO$_2$Phe-H)

According to the method described for 4b, saponification of 110 mg of 8ab with NaOH provided 83 mg of the carboxylic acid 8bb, which was reacted with N-methyl-N-tert-butylamine to provide 75 mg of 8cb. MS-ESI: [M+H]$^+$ 466.4.

8bb: NMR (DMSO-d$^6$) δ 1.01 (d, 6, isoC$_3$H$_7$), 2.91 (m, 4, CH$_2$CH$_2$), 3.78 (s, 3, OCH$_3$), 3.87 (m, 1, CH), 6.18 and 7.02 (2×m, 2, Ar—H) 7.40-7.53 and 7.64 (2×m, 4, FPhe-H).

8cb: NMR (DMSO-d$^6$) δ 1.02 (d, 6, isoC$_3$H$_7$), 1.45 (s, 9, tertC$_4$H$_9$), 2.68 and 2.88 (2×m, 4, CH$_2$CH$_2$), 3.02 (s, 3, NCH$_3$), 3.78 (s, 3, OCH$_3$), 3.90 (m, 1, CH), 6.22 and 7.02 (2×s, 2, Ar—H), 7.38-7.50 and 7.62 (2×m, 4, FPhe-H).

According to the method described for 4b, saponification of 104 mg of 8ac with NaOH provided 96 mg of the carboxylic acid 8bc, which was reacted with N-methyl-N-tert-butylamine to provide 50 mg of 8 cc. MS-ESI: [M+H]$^+$ 478.4.

8bc: NMR (DMSO-d$^6$) δ 1.00 (d, 6, isoC$_3$H$_7$), 2.90 (m, 4, CH$_2$CH$_2$), 3.76 and 3.79 (2×s, 6, OCH$_3$), 3.82 (m, 1, CH), 6.18 and 7.00 (2×m, 2, Ar—H) 7.08, 7.18 and 7.50 (3×m, 4, CH$_3$O-Phe-H).

8 cc: NMR (DMSO-d$^6$) δ 1.00 (d, 6, isoC$_3$H$_7$), 1.46 (s, 9, tertC$_4$H$_9$), 2.69 and 2.88 (2×m, 4, CH$_2$CH$_2$), 3.02 (s, 3, NCH$_3$), 3.76 and 3.78 (2×s, 3, OCH$_3$), 3.85 (m, 1, CH), 6.22 and 7.00 (2×s, 2, Ar—H), 7.07, 7.13 and 7.49 (3×m, 4, OCH$_3$Phe-H).

According to the method described for 4b, saponification of 70 mg of 8ad with NaOH provided 53 mg of the carboxylic acid 8bd, which was reacted with N-methyl-N-tert-butylamine to provide 35 mg of 8cd. MS-ESI: [M+H]$^+$ 462.33.

8bd: NMR (DMSO-d$^6$) δ 1.00 (d, 6, isoC$_3$H$_7$), 2.38 (s, 3, CH$_3$), 2.91 (m, 4, CH$_2$CH$_2$), 3.75 (s, 3, OCH$_3$), 3.80 (m, 1, CH), 6.16 and 7.00 (2×m, 2, Ar—H) 7.33, 7.40, 7.48, (3×m, 4, CH$_3$Phe-H).

8cd: NMR (DMSO-d$^6$) δ 1.00 (d, 6, isoC$_3$H$_7$), 1.45 (s, 9, tertC$_4$H$_9$), 2.37 (s, 3, CH$_3$), 2.70 and 2.88 (2×m, 4, CH$_2$CH$_2$), 3.03 (s, 3, NCH$_3$), 3.76 (s, 3, OCH$_3$), 3.83 (m, 1, CH), 6.20 and 7.00 (2×s, 2, Ar—H), 7.32, 7.38 and 7.47 (3×m, 4, CH$_3$Phe-H)

Example 9

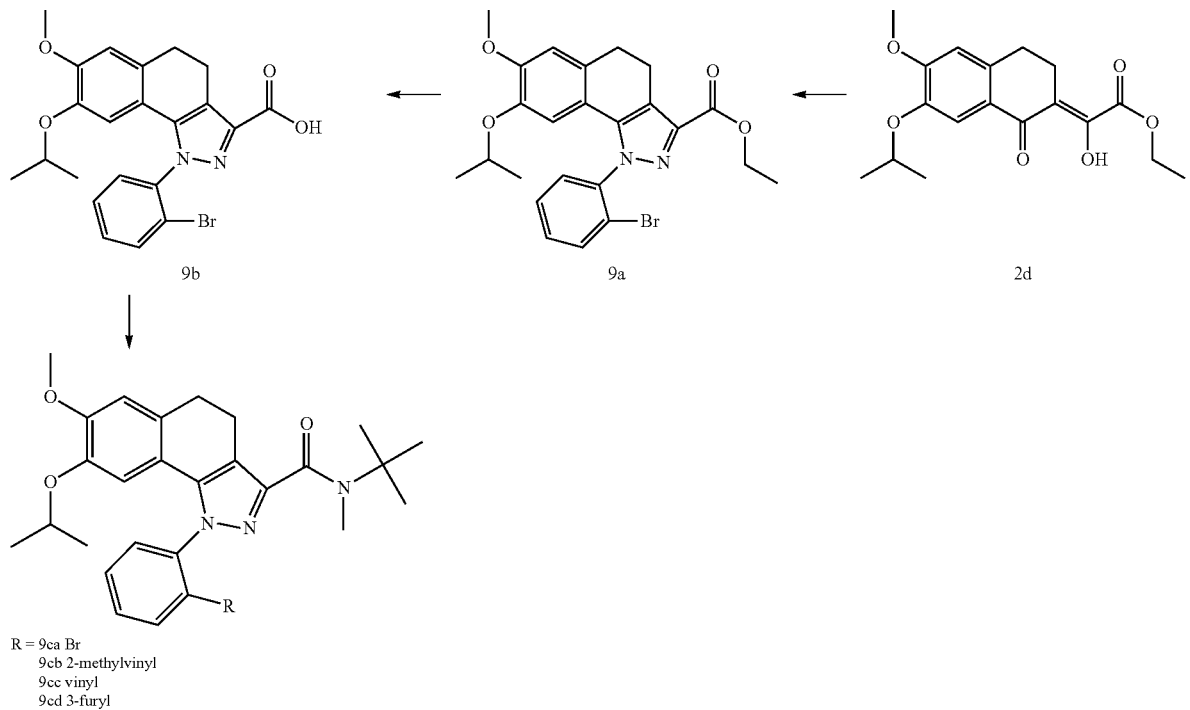

R = 9ca Br
9cb 2-methylvinyl
9cc vinyl
9cd 3-furyl 1-(2-bromophenyl)-N-tert-butyl-8-isopropoxy-7-methoxy-N-methyl-4,5-dihydro-1H-benzo[g]indazole-3-carboxamide 9ca 1-(2-(2-methyl-vinyl)-phenyl)-N-tert-butyl-8-isopropoxy-7-methoxy-N-methyl-4,5-dihydro-1H-benzo[g]indazole-3-carboxamide 9cb N-tert-butyl-8-isopropoxy-7-methoxy-N-methyl-1-(2-vinylphenyl)-4,5-dihydro-1H-benzo[g]indazole-3-carboxamide 9 cc N-tert-butyl-1-(2-(furan-3-yl)phenyl)-8-isopropoxy-7-methoxy-N-methyl-4,5-dihydro-1H-benzo[g]indazole-3-carboxamide 9cd Compound 9a was prepared from 2 g of 2d and 1.47 g of 2-bromophenyl hydrazine hydrochloride in acetic acid as described for 4a. The product was purified by chromatography, to provide 2.43 g of 9a; NMR (CDCl$_3$) δ 1.08 and 1.12 (2×d, 6, isoC3H7), 1.42 (t, 3, CH$_3$), 2.95 and 3.11 (3×m 4, CH$_2$CH$_2$), 3.85 (s, 3, OCH$_3$), 3.82 (m, 1, CH), 4.45 (q, 2, CH$_2$) 6.09 and 6.80 (2×s, 2, Ar—H), 7.42, 7.50, 7.59 and 7.74 (4×m, 4, oBrPhe-H). MS-ESI: [M+H]$^+$ 485.04 and 487.04.

According to the method described for 4b, saponification of 2.43 g of 9a with NaOH provided 2.2 g of the carboxylic acid 9b, which was reacted with N-methyl-N-tert-butylamine to provide 2.34 g of 9ca.

9b: NMR (CDCl$_3$) δ 1.10 and 1.08 (2×d, 6, isoC$_3$H$_7$), 2.97 and 3.12 (2×m, 4, CH$_2$CH$_2$), 3.85 (s, 3, OCH$_3$), 3.82 (m, 1, CH), 6.08 and 6.81 (2×m, 2, Ar—H) 7.45, 7.53 7.57 and 7.78 (4×m, 4, oBr-Phe-H). MS-ESI: [M+H]$^+$ 457.10 and 459.09.

9ca: NMR (CDCl$_3$) δ 1.08 and 1.11 (2×d, 6, isoC$_3$H$_7$), 1.53 (s, 9, tertC$_4$H$_9$), 2.88-3.00 (m, 4, CH$_2$CH$_2$), 3.14 (s, 3, NCH$_3$), 3.84 (s, 3, OCH$_3$), 3.82 (m, 1, CH), 6.08 and 6.80 (2×s, 2, Ar—H), 7.40, 7.47, 7.51 and 7.77 (4×m, 4, oBr-Phe-H). MS-ESI: [M+H]$^+$ 526.11 and 528.11.

A mixture of 25 mg of 9ca, 13 mg of K$_2$CO$_3$, 7 mg of 4,4,5,5-tetramethyl-2-(2-methyl-vinyl)-1,3,2-dioxaborolane and 5 mg of tetrakis(triphenylphosphine) palladium in 3 ml of degassed 90% aq. dimethoxyethane was heated in a sealed vessel under N$_2$ atmosphere for 16 hr at 90° C. as described for 7ca to give 9 mg of 9cb. MS-ESI: [M+H]$^+$ 488.4. NMR (CDCl$_3$) δ 1.05 and 1.07 (2×d, 6, isoC$_3$H$_7$), 1.53 (s, 9, tertC$_4$H$_9$), 1.69 and 1.61 (2×d, 3, CH$_3$), 2.90 (bd, 4, CH$_2$CH$_2$), 3.14 (s, 3, NCH$_3$), 3.82 (s, 3, OCH$_3$), 3.78 (m, 1, CH), 6.02 and 6.15 (2×m, 2, vinyl), 6.10 and 6.78 (2×s, 2, Ar—H), 7.32, 7.43, 7.65 (3×m, 4, phenyl-H).

A mixture of 25 mg of 9ca, 13 mg of K$_2$CO$_3$, 10 mg of 4,4,5,5-tetramethyl-2-(vinyl)-1,3,2-dioxaborolane and 5 mg of tetrakis(triphenylphosphine)palladium in 3 ml of degassed 90% aq. dimethoxyethane was heated in a sealed vessel under N$_2$ atmosphere for 16 hr at 90° C. as described for 7ca to give 10 mg of 9 cc. MS-ESI: [M+H]$^+$ 474.4. NMR (CDCl$_3$) δ 1.05 and 1.07 (2×d, 6, isoC$_3$H$_7$), 1.53 (s, 9, tertC$_4$H$_9$), 1.69 and 1.61 (2×d, 3, CH$_3$), 2.93 (bd, 4, CH$_2$CH$_2$), 3.14 (s, 3, NCH$_3$), 3.82 (s, 3, OCH$_3$), 3.78 (m, 1, CH), 5.20 (d, 1, vinyl), 5.65 (d, 1, vinyl) and 6.33 (dd, 1, vinyl), 6.08 and 6.78 (2×s, 2, Ar—H), 7.40, 750, 7.73 (3×m, 4, phenyl-H).

A mixture of 25 mg of 9ca, 13 mg of K$_2$CO$_3$, 10 mg of 4,4,5,5-tetramethyl-2-(3-furyl)-1,3,2-dioxaborolane and 5 mg of tetrakis (triphenylphosphine) palladium in 3 ml of degassed 90% aq. dimethoxyethane was heated in a sealed vessel under N$_2$ atmosphere for 16 hr at 90° C. as described for 7ca to give 12 mg of 9cd. MS-ESI: [M+H]$^+$ 514.4.

NMR (CDCl$_3$) δ 1.05 and 1.10 (2×d, 6, isoC$_3$H$_7$), 1.52 and 1.54 (2×s, 9, tertC$_4$H$_9$), 2.80-3.00 (bm, 4, CH$_2$CH$_2$), 3.04 (s, 3, NCH$_3$), 3.81 (s, 3, OCH$_3$), 3.77 (m, 1, CH), 6.12 and 6.53 (2×s, 2, Ar—H) 6.16 and 6.90 and 7.25 (3×m, 3,3-furyl-H), 7.40-7.65 (m, 4, phenyl-H).

Example 10

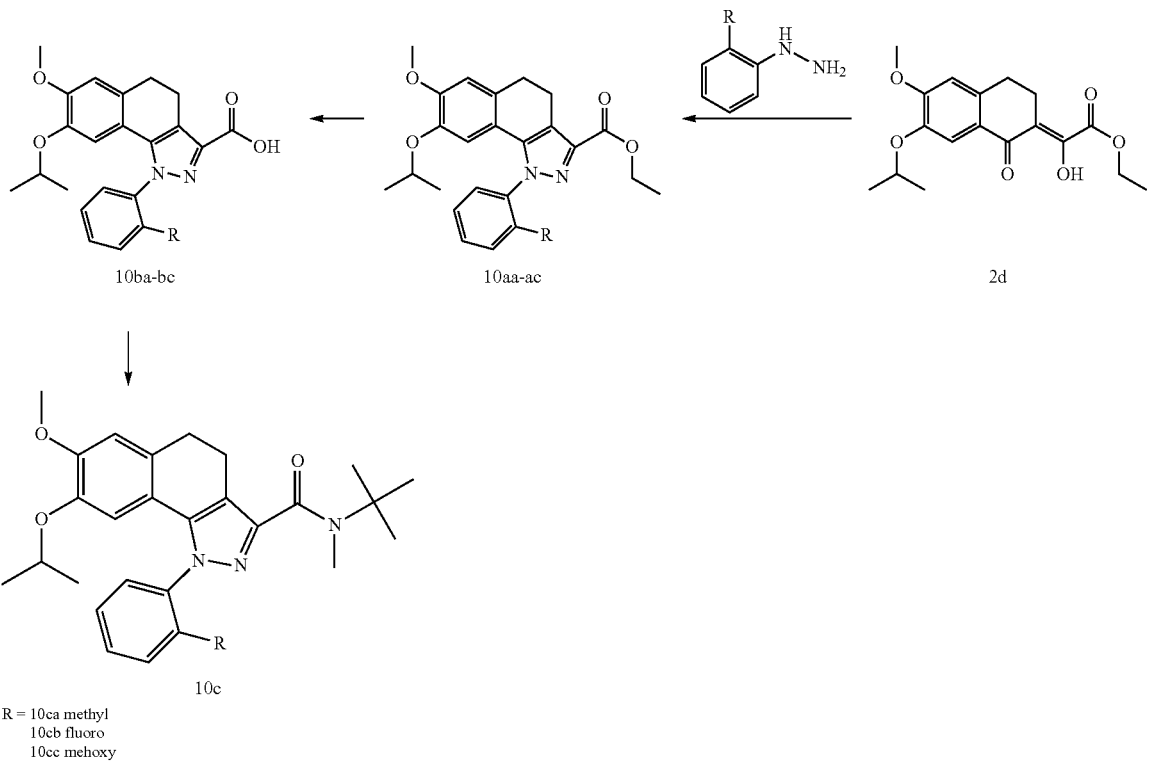

R = 10ca methyl
10cb fluoro
10cc mehoxy

N-tert-butyl-8-isopropoxy-7-methoxy-N-methyl-1-o-tolyl-4,5-dihydro-1H-benzo[g]indazole-3-carboxamide 10ca
N-tert-butyl-1-(2-fluorophenyl)-8-isopropoxy-7-methoxy-N-methyl-4,5-dihydro-1H-benzo[g]indazole-3-carboxamide 10cb
N-tert-butyl-8-isopropoxy-7-methoxy-1-(2-methoxyphenyl)-N-methyl-4,5-dihydro-1H-benzo[g]indazole-3-carboxamide 10 cc Compound 10aa was prepared from 100 mg of 2d and 40 mg of 2-methylphenyl hydrazine hydrochloride in acetic acid as described for 4a. The product was purified by chromatography, to provide 100 mg of 10aa; NMR (CDCl$_3$) δ 1.02 and 1.07 (2×d, 6, isoC$_3$H$_7$), 1.43 (t, 3, CH$_3$), 2.03 (s, 3, CH$_3$), 2.92 and 3.10 (2×m 4, CH$_2$CH$_2$), 3.83 (s, 3, OCH$_3$), 3.75 (m, 1, CH), 4.44 (q, 2, CH$_2$) 6.08 and 6.78 (2×s, 2, Ar—H), 7.30-7.45 (m, 4, oCH$_3$Phe-H). MS-ESI: [M+H]$^+$ 421.16.

Compound 10ab was prepared from 100 mg of 2d and 41 mg of 2-fluorophenyl hydrazine hydrochloride in acetic acid as described for 4a. The product was purified by chromatography, to provide 98 mg of 10ab; NMR (CDCl$_3$) δ 1.10 (bd, 6, isoC$_3$H$_7$), 1.42 (t, 3, CH$_3$), 2.96 and 3.18 (2×m, 4, CH$_2$CH$_2$), 3.85 (s, 3, OCH$_3$), 3.88 (m, 1, CH), 4.45 (q, 2, CH$_2$) 6.25 and 6.81 (2×s, 2, Ar—H), 7.26, 7.33, 7.52, 7.60 (4×m, 4, oFPhe-H). MS-ESI: [M+H]$^+$ 425.21.

Compound 10ac was prepared from 100 mg of 2d and 45 mg of 2-methoxyphenyl hydrazine hydrochloride in acetic acid as described for 4a. The product was purified by chromatography, to provide 35 mg of 10ac; NMR (CDCl$_3$) δ 1.08 (dd, 6, isoC$_3$H$_7$), 1.42 (t, 3, CH$_3$), 2.90-3.20 (bm 4, CH$_2$CH$_2$), 3.69 (s, 3, OCH$_3$), 3.81 (m, 1, CH), 3.84 (s, 3, OCH$_3$), 4.43 (q, 2, CH$_2$) 6.24 and 6.78 (2×s, 2, Ar—H), 7.05, 7.09, 7.46, 7.50 (4×m, 4, oCH$_3$OPhe-H). MS-ESI: [M+H]$^+$ 437.25

According to the method described for 4b, saponification of 95 mg of 10aa with NaOH provided 90 mg of the carboxylic acid 10ba, which was reacted with N-methyl-N-tert-butylamine to provide 25 mg of 10ca.

10ba: NMR (CDCl$_3$) δ 1.06 (2×d, 6, isoC$_3$H$_7$), 2.04 (s, 3, CH$_3$), 2.94 and 3.12 (2×m, 4, CH$_2$CH$_2$), 3.83 (s, 3, OCH$_3$), 3.75 (m, 1, CH), 6.08 and 6.80 (2×m, 2, Ar—H) 7.39, 7.47 (2×m, 4, oCH$_3$Phe-H). MS-ESI: [M+H]$^+$ 393.20.

10ca: NMR (CDCl$_3$) δ 1.06 (d, 6, isoC$_3$H$_7$), 1.55 (s, 9, tertC$_4$H$_9$), 2.07 (s, 3, CH$_3$), 2.92 (m, 4, CH$_2$CH$_2$), 3.12 (s, 3, NCH$_3$), 3.82 (s, 3, OCH$_3$), 3.78 (m, 1, CH), 6.09 and 6.78 (2×s, 2, Ar—H), 7.30-7.45 (4×m, 4, CH$_3$Phe-H). MS-ESI: [M+H]$^+$ 462.40.

According to the method described for 4b, saponification of 97 mg of 10ab with NaOH provided 88 mg of the carboxylic acid 10bb, which was reacted with N-methyl-N-tert-butylamine to provide 27 mg of 10cb.

10bb: NMR (CDCl$_3$) δ 1.10 (bd, 6, isoC$_3$H$_7$), 2.88-3.22 (bm, 4, CH$_2$CH$_2$), 3.84 (s, 3, OCH$_3$), 3.88 (m, 1, CH), 6.35 and 6.82 (2×m, 2, Ar—H) 7.28, 7.36 7.55 and 7.59 (4×m, 4, oFPhe-H). MS-ESI: [M+H]$^+$ 397.20.

10cb: NMR (CDCl$_3$) δ 1.10 (bd, 6, isoC$_3$H$_7$), 1.56 (s, 9, tertC$_4$H$_9$), 2.85-3.00 (m, 4, CH$_2$CH$_2$), 3.12 (s, 3, NCH$_3$), 3.83 (s, 3, OCH$_3$), 3.87 (m, 1, CH), 6.27 and 6.80 (2×s, 2, Ar—H), 7.22-7-32 and 7.45-7.58 (2×m, 4, oFPhe-H). MS-ESI: [M+H]$^+$ 466.28.

According to the method described for 4b, saponification of 35 mg of 10ac with NaOH provided 31 mg of the carboxylic acid 10bc, which was reacted with N-methyl-N-tert-butylamine to provide 25 mg of 10cc.

10bc: NMR (CDCl$_3$) δ 1.09 (2×d, 6, isoC$_3$H$_7$), 2.90-3.20 (bm, 4, CH$_2$CH$_2$), 3.51 (s, 3, OCH$_3$), 3.84 (s, 3, OCH$_3$), 3.81 (m, 1, CH), 6.32 and 6.79 (2×m, 2, Ar—H) 7.08, 7.12, 7.45 and 7.52 (4×m, 4, oCH$_3$OPhe-H). MS-ESI: [M+H]$^+$ 409.21.

10 cc: NMR (CDCl$_3$) δ 1.08 (2×d, 6, isoC$_3$H$_7$), 1.55 (s, 9, tertC$_4$H$_9$), 2.92 (m, 4, CH$_2$CH$_2$), 3.05 (s, 3, NCH$_3$), 3.68 (s, 3, OCH$_3$), 3.83 (s, 3, OCH$_3$), 3.82 (m, 1, CH), 6.23 and 6.78 (2×s, 2, Ar—H), 7.06 and 7.43 (2×m, 4, oCH$_3$OPhe-H). MS-ESI: [M+H]$^+$ 4.78.40.

Example 11

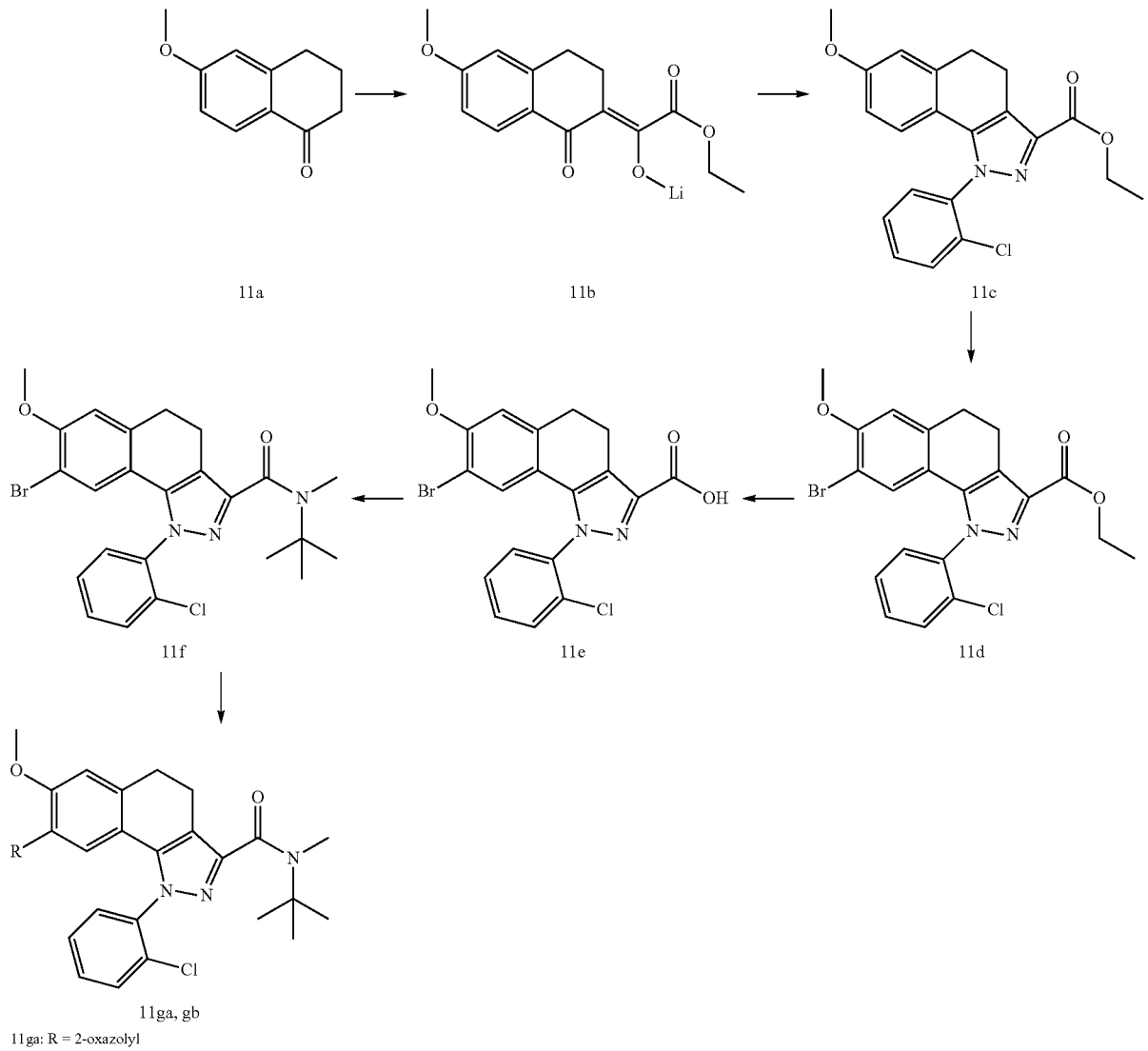

11ga: R = 2-oxazolyl
11gb: R = 3-pyridyl

N-tert-butyl-1-(2-chlorophenyl)-7-methoxy-N-methyl-8-(oxazol-2-yl)-4,5-dihydro-1H-benzo[g]indazole-3-carboxamide 11ga N-tert-butyl-1-(2-chlorophenyl)-7-methoxy-N-methyl-8-(pyridin-3-yl)-4,5-dihydro-1H-benzo[g]indazole-3-carboxamide 11gb To a solution of 5 g of 6-methoxytetralone (11a) and 4.46 ml of diethyl oxalate in 100 ml of dry diethyl ether was added dropwise at 0° C., under a nitrogen atmosphere, 32.6 ml of a 1M solution of lithium bistrimethylsilyl amide. The cooling device was removed and the reaction mixture was stirred for 2 hr at ambient temperature. The solid formed was filtered and washed with dry ether and dried, to provide 7.6 g of 11b.

NMR (CDCl$_3$) δ 1.20 (t, 3, CH$_3$), 2.64 and 2.85 (2×m, 4, CH$_2$CH$_2$), 3.80 (s, 3, OCH$_3$), 4.11 (q, 2, CH$_2$), 6.53 (s, 1, Ar—H), 6.62 (d, 1, Ar—H), 7.88 (d, 1, Ar—H).

A mixture of 250 mg of 11b, 110 mg of o-Cl-phenyl hydrazine hydrochloride and 3 ml of acetic acid was heated at 100° C. for 16 hr. The reaction mixture was cooled, diluted with 10 ml of water and neutralized by addition of cold conc. aq. NH$_4$OH. The product was extracted into ethyl acetate. The organic extract was dried and concentrated and the crude product was purified by chromatography over silica gel, using a gradient of toluene/ethyl acetate as eluent, to provide 180 mg of 11e; MS-ESI: [M+H]$^+$ 383.15. NMR (CDCl$_3$) δ 1.42 (t, 3, CH$_3$), 2.95-3.18 (2bm, 4, CH$_2$CH$_2$), 3.78 (s, 3, OCH$_3$), 4.45 (q, 2, CH$_2$) 6.25 and 6.45 and 6.50 (AB, 2, Ar—H), 6.83 (d, 1, Ar—H) 7.42-7.58, (m, 4, oClPhe-H).

A solution of 75 mg of 11c in 2.5 ml of acetic acid was treated with a solution of 25 μl of bromine in 1 ml of acetic acid. After stirring for 3 hr, the mixture was poured into water and treated with 0.5 ml of sat. aq. Na$_2$SO$_3$ and neutralized by addition of cold conc. aq. NH$_4$OH. The product was extracted into ethyl acetate. The extract was washed, dried, concentrated and the crude material was purified by chromatography over silica gel, using a gradient of toluene/ethyl acetate to provide 45 mg of 11d; MS-ESI: [M+H]$^+$ 461.07, 463.05. NMR (CDCl$_3$) δ 1.43 (t, 3, CH$_3$), 3.01 and 3.22 (2×m, 4, CH$_2$CH$_2$), 3.90 (s, 3, OCH$_3$), 4.45 (q, 2, CH$_2$), 6.61 and 6.84 (2×s, 2, Ar—H), 7.45-7.60 (m, 4, oClPhe).

A solution of 112 mg of 11d in 3 ml of ethanol and 2 ml of 2N NaOH was mixed and the mixture was heated at 60° C. for 1 hr. The reaction mixture was cooled and neutralized with cold 1N HCl and the product was extracted into ethyl acetate. The organic layer was washed, dried and concentrated, to provide 100 mg of essentially pure material 11e; MS-ESI: [M+H]$^+$ 433.05 and 435.05. NMR (CDCl$_3$) δ 2.95-3.30 (bm, 4, CH$_2$CH$_2$), 3.90 (s, 3, OCH$_3$), 6.61 and 6.85 (2×s, 2, Ar—H), 7.50-7.65 (m, 4, oClPhe).

A mixture consisting of 100 mg of 11e, 200 µl of DiPEA, 120 mg of TBTU, 0.5 ml of DMF and 2 ml of dichloromethane was stirred for 0.5 hr at RT. Then, 50 µl of N-methyl-N-tert-butylamine was added and stirring was prolonged for 16 hr. To the mixture was added 10 ml of water and the product was extracted with dichloromethane. The organic layer was dried and concentrated and the product was chromatographed over silica gel, using a gradient of heptane/ethyl acetate as eluent, to provide 65 mg of 11f; MS-ESI: [M+H]$^+$ 502.30 and 504.30. NMR (CDCl$_3$) δ 1.53 (s, 9, tertC$_4$H$_9$), 2.97 (m, 4, CH$_2$CH$_2$), 3.14 (s, 3, NCH$_3$), 3.79 (s, 3, OCH$_3$), 6.61 and 6.83 (2×s, 2, Ar—H), 7.43-7.62 (4×m, 4, oCl-Phe-H).

A solution of 21 mg of 11f, 20 µl of 2-tributylstannyl oxazole and 4 mg of tetrakis(triphenylphosphine) palladium in 2 ml of degassed toluene, was heated under N$_2$ atmosphere for 16 hr at 105° C. The reaction mixture was then concentrated and the isolated material was purified by chromatography over silica gel, using a gradient of toluene/ethyl acetate to provide 4 mg of 11ga; MS-ESI: [M+H]$^+$ 491.23. NMR (CDCl$_3$) δ 1.54 (s, 9, tertC$_4$H$_9$), 3.00 and 3.07 (2×m, 4, CH$_2$CH$_2$), 3.17 (s, 3, NCH$_3$), 3.98 (s, 3, OCH$_3$), 6.97 and 7.50 (2×s, 2, Ar—H), 7.12 and 7.17 (2×s, 2, oxazole-H), 7.42-7.70 (4×m, 4, oClPhe-H).

A mixture of 21 mg of 11f, 12 mg of K$_2$CO$_3$, 8 mg of pyridine-3-boronic acid and 5 mg of tetrakis(triphenylphosphine) palladium in 3 ml of degassed 90% aq. dimethoxyethane was heated in a sealed vessel under N$_2$ atmosphere for 16 hr at 90° C. The reaction mixture was cooled to RT and diluted with 5% K$_2$CO$_3$ solution and the product was extracted with ethyl acetate. The extract was washed, dried, concentrated and the crude material was purified by chromatography over silica gel, using a gradient of toluene/ethyl acetate to provide 12.9 mg of 11gb; MS-ESI: [M+H]$^+$ 501.3. NMR (CDCl$_3$) δ 1.53 (s, 9, tertC$_4$H$_9$), 2.95-3.07 (bm, 4, CH$_2$CH$_2$), 3.17 (s, 3, NCH$_3$), 3.83 (s, 3, OCH$_3$), 6.47 and 7.20 (2×s, 2, Ar—H), 7.20-8.32, 8.45 (3×m, 3, pyridine-H), 7.42-7.70 (5×m, 4, oClPhe-H+pyridine-H).

Example 12

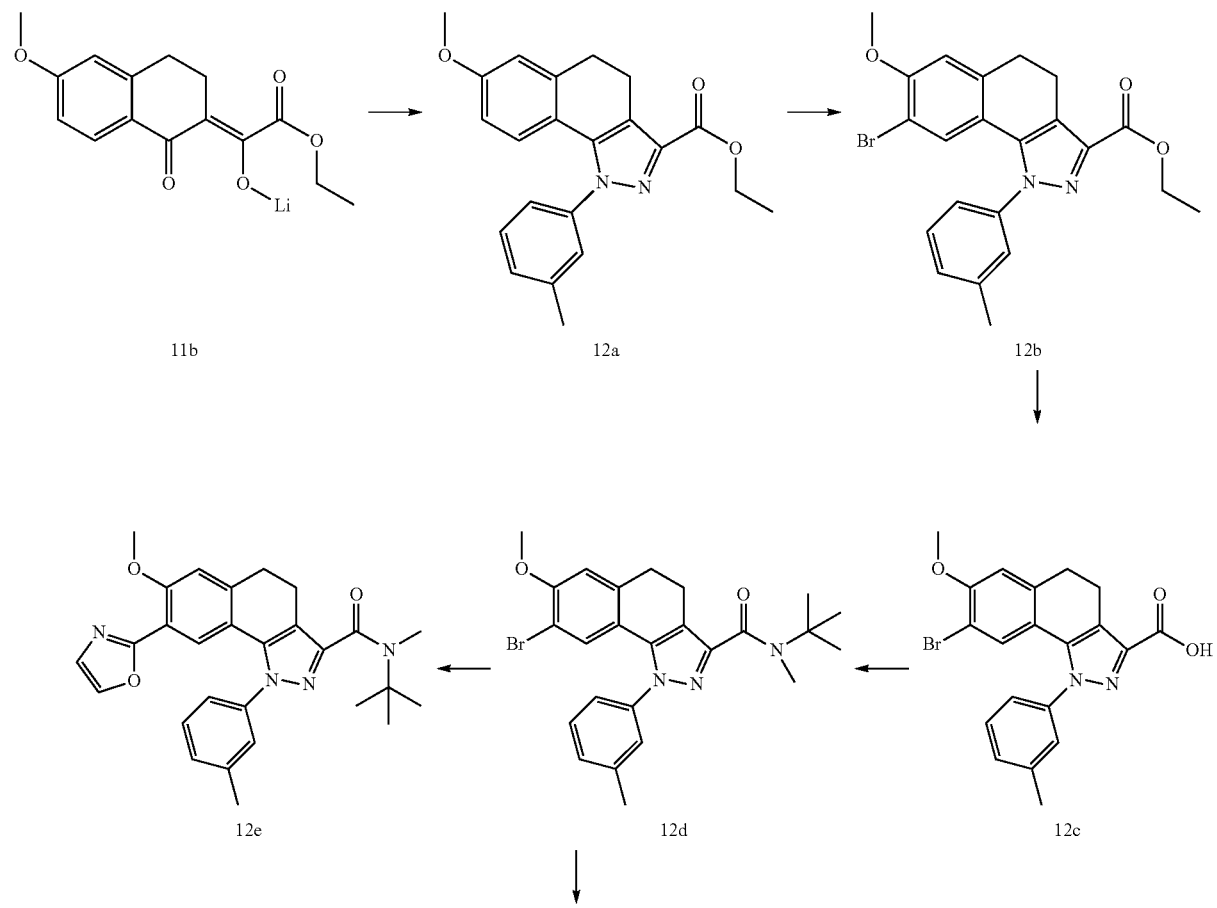

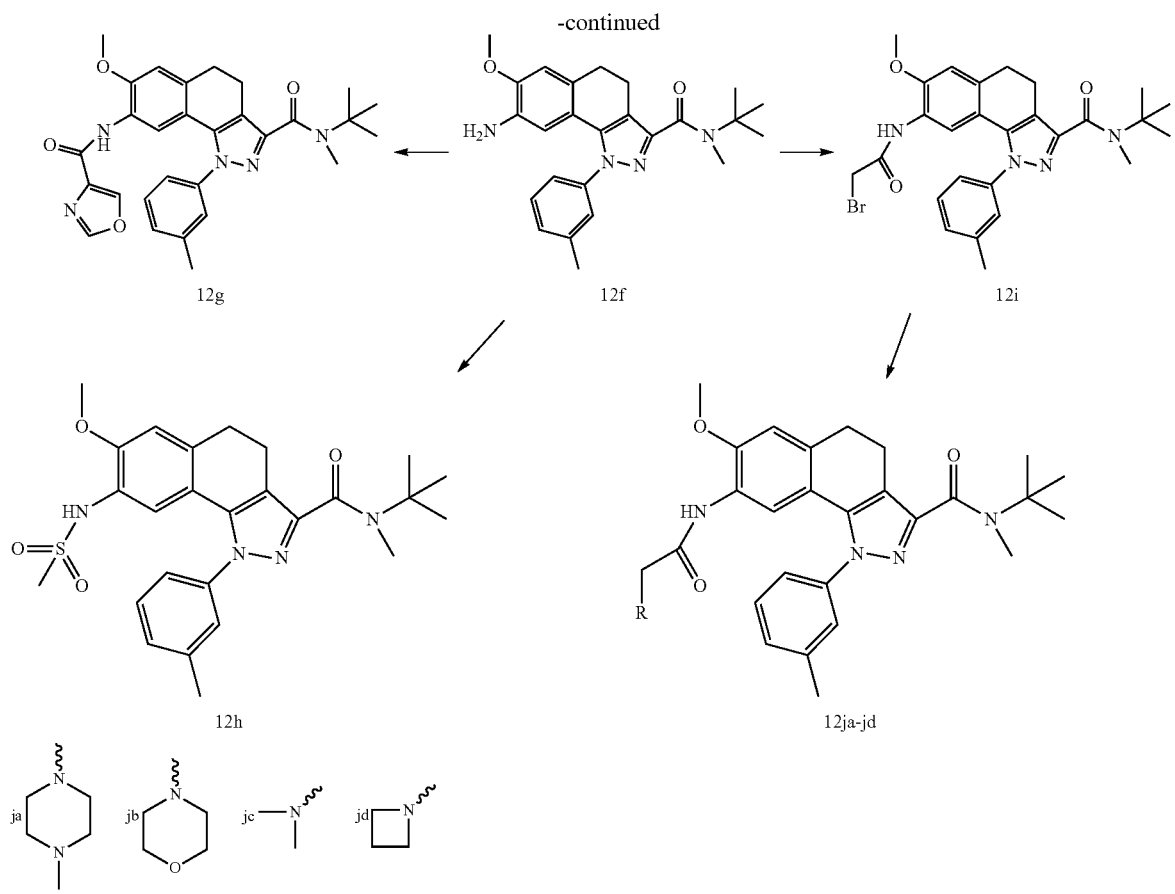

8-(2-(azetidin-1-yl)acetamido)-N-tert-butyl-7-methoxy-N-methyl-1-m-tolyl-4,5-dihydro-1H-benzo[g]indazole-3-carboxamide 12jd N-tent-butyl-8-(2-(dimethylamino)acetamido)-7-methoxy-N-methyl-1-m-tolyl-4,5-dihydro-1H-benzo[g]indazole-3-carboxamide 12jc N-tert-butyl-7-methoxy-N-methyl-8-(2-morpholinoacetamido)-1-m-tolyl-4,5-dihydro-1H-benzo[g]indazole-3-carboxamide 12jb N-tent-butyl-7-methoxy-N-methyl-8-(2-(4-methylpiperazin-1-yl)acetamido)-1-m-tolyl-4,5-dihydro-1H-benzo[g]indazole-3-carboxamide 12ja A solution of 500 mg of 11b and 310 mg of m-methylphenylhydrazine hydrochloride in 5 ml of acetic acid was treated as indicated for example 11c, to provide 530 mg of 12a; MS-ESI: [M+H]+ 363.16. NMR (CDCl$_3$) δ 1.43 (t, 3, CH$_3$), 2.40 (s, 3, CH$_3$), 2.98 and 3.08 (2×m, 4, CH$_2$CH$_2$), 3.79 (s, 3, OCH$_3$), 4.44 (q, 2, CH$_2$), 6.52 and 6.70 (AB, 2, Ar—H), 6.85 (d, 1, Ar—H) 7.26-7.38, (m, 4, mCH$_3$Phe-H).

A solution of 475 mg of 12a in 20 ml of acetic acid was brominated as indicated for the conversion of 11c to 11d, to provide 538 mg of 12b; MS-ESI: [M+H]+ 441.03 and 443.05. NMR (CDCl$_3$) δ 1.42 (t, 3, CH$_3$), 2.42 (s, 3, CH$_3$), 2.97 and 3.09 (2×m, 4, CH$_2$CH$_2$), 3.91 (s, 3, OCH$_3$), 4.44 (q, 2, CH$_2$), 6.85 and 6.91 (2×s, 2, Ar—H), 7.23-7.40, (m, 4, mCH$_3$Phe-H).

The carboxylic acid 12c was obtained by saponification with NaOH as exemplified by the conversion of 11d into 11e. Conversion of 60 mg of 12b provided 37 mg of the carboxylic acid 12c; MS-ESI: [M+H]+ 413.04 and 415.02. NMR (CDCl$_3$) δ 2.43 (s, 3, CH3), 2.98 and 3.10 (2×m, 4, CH$_2$CH$_2$), 3.92 (s, 3, OCH$_3$), 6.86 and 6.92 (2×s, 2, Ar—H), 7.27-7.43, (m, 4, mCH$_3$Phe-H).

The conversion of 36 mg of 12c into 33 mg of 12d was accomplished according to the method described for 11f. MS-ESI: [M+H]+ 482.12 and 484.11. NMR (CDCl$_3$) δ 1.52 (s, 9, tertC$_4$H$_9$), 2.43 (s, 3, CH$_3$), 2.90 and 3.06 (2×m, 4, CH$_2$CH$_2$), 3.05 (s, 3, NCH$_3$), 3.90 (s, 3, OCH$_3$), 6.84 and 6.94 (2×s, 2, Ar—H), 7.20-7.40 (4×m, 4, mCH$_3$Phe-H).

A Stille coupling of 32 mg of 12d with 30 μl of 2-(tributylstannyl) oxazole was carried out as described for the conversion of 11f to 11ge, to provide 8 mg of 12e; MS-ESI: [M+H]+ 471.19. NMR (CDCl$_3$) δ 1.53 (s, 9, tertC$_4$H$_9$), 2.40 (s, 3, CH$_3$), 2.95 and 3.07 (2×m, 4, CH$_2$CH$_2$), 3.17 (s, 3, NCH$_3$), 3.98 (s, 3, OCH$_3$), 6.98 and 7.52 (2×s, 2, Ar—H), 7.18 and 7.42 (2×s, 2, oxazole-H), 7.25-7.35 (4×m, 4, oCH$_3$-Phe-H).

A mixture of 514 mg of 12d, 323 mg of aminotriphenyl silane, 1.3 ml of a 1M solution of lithiumbistrimethyl amide (in THF), 30 mg of 2-(dicyclohexylphosphino) biphenyl and 30 mg of tris(dibenzylideneacetone) palladium in 25 ml of dry, degassed toluene was heated at 100° C. for 4 hr, under a N$_2$ atmosphere. The reaction mixture was cooled and poured into a 5% aq. NH$_4$Cl solution and extracted with ethyl acetate. The extract was dried, concentrated and the crude material was purified by chromatography over silica gel, using a gradient of toluene/ethyl acetate as eluent, to give 145 mg of 12f; MS-ESI: [M+H]+ 419.15. NMR (CDCl$_3$) δ 1.52 (s, 9, tertC$_4$H$_9$), 2.40 (s, 3, CH$_3$), 2.84 and 2.90 (2×m, 4, CH$_2$CH$_2$), 3.12 (s, 3, NCH$_3$), 3.87 (s, 3, OCH$_3$), 6.18 and 6.72 (2×s, 2, Ar—H), 7.20-7.35 (4×m, 4, mCH$_3$Phe-H).

A solution of 4-oxazole carboxylic acid, 12 µl of DiPEA and 25 mg of TBTU in 1 ml of dichloromethane was stirred for 15 min, then 21 mg of 12f was added, and the reaction mixture was stirred for 16 hr. Then water was added and the organic layer was separated and washed with water, dried and concentrated and the residue was purified over a silica gel column, using a gradient of toluene and ethyl acetate as eluent, to provide 15 mg of 12g; MS-ESI: [M+H]$^+$ 514.3. NMR (CDCl$_3$) δ 1.52 (s, 9, tertC$_4$H$_9$), 2.38 (s, 3, CH$_3$), 2.85 and 2.95 (2×m, 4, CH$_2$CH$_2$), 3.14 (s, 3, NCH$_3$), 3.97 (s, 3, OCH$_3$), 6.86, 7.86, 8.01 and 8.21, (4×s, 4, ArH+oxazole-H), 7.20-7.40 (4×m, 4, mCH$_3$Phe-H), 9.08 (bs, 1, NH).

To a solution of 19 mg of 12f and 10 µl of triethylamine in 0.2 ml of dichloromethane was added a solution of 5 µl of methanesulfonyl chloride in 0.1 ml of dichloromethane.

The reaction mixture was stirred for 5 hr and then 2 ml of 5% aq. NaHCO$_3$ was added and the product was extracted into dichloromethane. The extract was dried and concentrated and the product was purified by chromatography over silica gel, using a gradient of heptane/ethylacetate as eluent. This provided 9 mg of 12h; MS-ESI: [M+H]$^+$ 497.3. NMR (CDCl$_3$) δ 1.54 (s, 9, tertC$_4$H$_9$), 2.40 (s, 3, CH$_3$), 2.72 (s, 3, CH$_3$SO$_2$), 2.90 and 2.98 (2×m, 4, CH$_2$CH$_2$), 3.15 (s, 3, NCH$_3$), 3.88 (s, 3, OCH$_3$), 6.84, 6.90, (2×s, 2, Ar—H), 7.20-7.40 (4×m, 4, mCH$_3$Phe-H), 6.56 (bs, 1, NH).

To a solution of 145 mg of 12f and 200 µl of DiPEA in 10 ml of dichloromethane was added dropwise 50 µl of bromoacetyl bromide in 1 ml of dichloromethane. The reaction mixture was stirred for 4 hr and then quenched by pouring into 10 ml of sat. aq. NaHCO$_3$. The organic layer was separated, dried, concentrated and the product was purified by chromatography over silica gel, using a gradient of heptane/ethylacetate, to give 95 mg of 12i. NMR (CDCl$_3$) δ 1.52 (s, 9, tertC$_4$H$_9$), 2.40 (s, 3, CH$_3$), 2.88 and 2.95 (2×m, 4, CH$_2$CH$_2$), 3.14 (s, 3, NCH$_3$), 3.92 (s, 3, OCH$_3$), 4.05 (s, 2, CH$_2$), 6.84, 7.88, (2×s, 2, Ar—H), 7.25-7.40 (4×m, 4, mCH$_3$Phe-H), 8.70 (bs, 1, NH).

A mixture of 21 mg of 12i, 20 µl of DiPEA and 20 µl of 1-methylpiperazine in 0.3 ml of dichloromethane was stirred for 16 hr at RT. The reaction mixture was diluted with 2 ml of 5% aq. NaHCO$_3$ and the product was extracted into dichloromethane. The extract was washed several times with water, dried and concentrated. The crude material was purified by chromatography on silica gel, using a gradient of toluene/acetone, to provide 5 mg of 12ja; MS-ESI: [M+H]$^+$ 559.3. NMR (CDCl$_3$) δ 1.53 (s, 9, tertC$_4$H$_9$), 2.30 (s, 3, NCH$_3$), 2.40 (s, 3, CH$_3$), 2.88 and 2.96 (2×m, 4, CH$_2$CH$_2$), 3.14 (s, 3, NCH$_3$), 3.91 (s, 3, OCH$_3$), 6.82, 7.92, (2×s, 2, Ar—H), 7.22-7.40 (4×m, 4, mCH$_3$Phe-H), 9.55 (bs, 1, NH).

In a similar way as described for the conversion of 12i to 12 ja, 19 mg of 12i was converted into 7.5 mg of 12jb; MS-ESI: [M+H]$^+$ 546.4. NMR (CDCl$_3$) δ 1.53 (s, 9, tertC$_4$H$_9$), 2.56 (m, 4, morpholino CH$_2$), 2.40 (s, 3, CH$_3$), 2.88 and 2.96 (2×m, 4, CH$_2$CH$_2$), 3.02 (s, 2, CH$_2$), 3.15 (s, 3, NCH$_3$), 3.74 (m, 4, CH$_2$ morpholino), 3.91 (s, 3, OCH$_3$), 6.82, 7.91, (2×s, 2, Ar—H), 7.26-7.40 (4×m, 4, mCH$_3$Phe-H), 9.52 (bs, 1, NH).

In a similar way as described for the conversion of 12i to 12 ja, 19 mg of 12i was converted into 8 mg of 12jc; MS-ESI: [M+H]$^+$ 504.4. NMR (CDCl$_3$) δ 1.53 (s, 9, tertC$_4$H$_9$), 2.30 (s, 6, N,N-dimethyl), 2.39 (s, 3, CH$_3$), 2.87 and 2.95 (2×m, 4, CH$_2$CH$_2$), 2.95 (s, 2, CH$_2$), 3.15 (s, 3, NCH$_3$), 3.89 (s, 3, OCH$_3$), 6.82, 7.90, (2×s, 2, Ar—H), 7.26-7.40 (4×m, 4, mCH$_3$Phe-H), 9.30 (bs, 1, NH).

In a similar way as described for the conversion of 12i to 12 ja, 19 mg of 12i was converted into 6 mg of 12jd; MS-ESI: [M+H]$^+$ 516.4. NMR (CDCl$_3$) δ 1.53 (s, 9, tertC$_4$H$_9$), 2.31 (m, 2, azetidine CH$_2$), 2.40 (s, 3, CH$_3$), 2.88 and 2.95 (2×m, 4, CH$_2$CH$_2$), 3.10 (s, 2, CH$_2$), 3.13 (s, 3, NCH$_3$), 3.32 (m, 4, 2×CH$_2$ azetidine), 3.92 (s, 3, OCH$_3$), 6.82, 7.90, (2×s, 2, Ar—H), 7.26-7.40 (4×m, 4, mCH$_3$Phe-H), 9.20 (bs, 1, NH).

Example 13

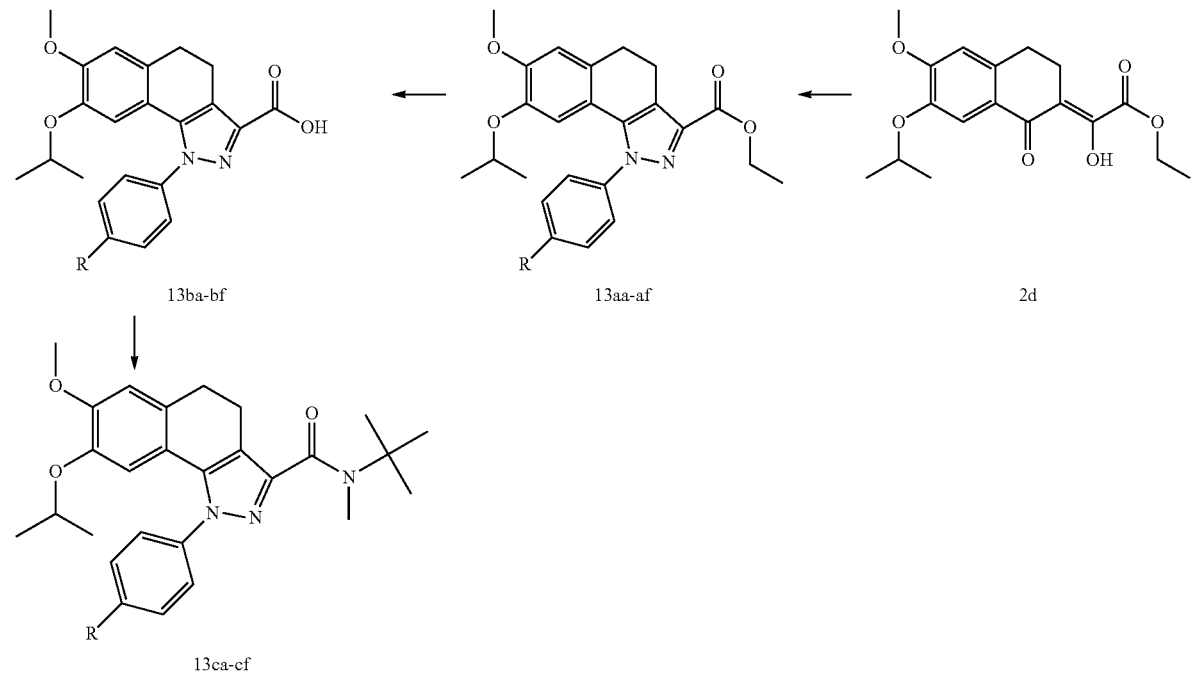

R = 13ca CH$_3$
13cb C$_2$H$_5$
13cc OCH$_3$
13cd F
13ce Cl
13cf Br

N-tert-butyl-8-isopropoxy-7-methoxy-N-methyl-1-p-tolyl-4,5-dihydro-1H-benzo[g]indazole-3-carboxamide 13ca N-tert-butyl-1-(4-ethylphenyl)-8-isopropoxy-7-methoxy-N-methyl-4,5-dihydro-1H-benzo[g]indazole-3-carboxamide 13cb N-tert-butyl-8-isopropoxy-7-methoxy-1-(4-methoxyphenyl)-N-methyl-4,5-dihydro-1H-benzo[g]indazole-3-carboxamide 13 cc N-tert-butyl-1-(4-fluorophenyl)-8-isopropoxy-7-methoxy-N-methyl-4,5-dihydro-1H-benzo[g]indazole-3-carboxamide 13cd N-tert-butyl-1-(4-chlorophenyl)-8-isopropoxy-7-methoxy-N-methyl-4,5-dihydro-1H-benzo[g]indazole-3-carboxamide 13ce N-tert-butyl-1-(4-bromophenyl)-8-isopropoxy-7-methoxy-N-methyl-4,5-dihydro-1H-benzo[g]indazole-3-carboxamide 13cf Compound 13aa was prepared from 90 mg of 2d and 48 mg of 4-methylphenyl hydrazine hydrochloride in acetic acid as described for 4a. The product was purified by chromatography, to give 46 mg of 13aa; NMR (CDCl$_3$) δ 1.10 (d, 6, isoC$_3$H$_7$), 1.42 (t, 3, CH$_3$), 2.43 (s, 3, CH$_3$), 2.93 and 3.08 (2×t, 4, CH$_2$CH$_2$), 3.86 (s, 3, OCH$_3$ and m, 1, CH), 4.44 (q, 2, CH$_2$) 6.24 and 6.80 (2×s, 2, Ar—H), 7.30 and 7.40 (2×dd, 4, CH$_3$Phe-H).

Compound 13aa was saponified to the carboxylic acid, by heating with NaOH in aqueous ethanol according the method described in example for 4b, to give 40 mg of 13ba; MS-ESI: [M+H]$^+$ 393.11. NMR (DMSO-d$^6$) δ 0.99 (d, 6, isoC$_3$H$_7$), 2.42 (s, 3, CH$_3$), 2.90 (m, 4, 2×CH$_2$CH$_2$), 3.73 (s, 3, OCH$_3$), 3.77 (m, 1, CH), 6.10 and 6.99 (2×m, 2, Ar—H), 7.40 (bs, 4, CH$_3$Phe-H).

The carboxylic acid was converted into the amide by reaction with N-methyl-N-tert-butylamine according to the method described for 4d, to provide 22 mg of 13ca; MS-ESI: [M+H]$^+$ 462.19. NMR (DMSO-d$^6$) δ 1.00 (d, 6, isoC$_3$H$_7$), 1.43 (s, 9, tertC$_4$H$_9$), 2.41 (s, 3, CH$_3$) 2.70 and 2.86 (2×m, 4, CH$_2$CH$_2$), 3.02 (s, 3, NCH$_3$), 3.75 (s, 3, OCH$_3$), 3.80 (m, 1, CH), 6.13 and 7.00 (2×s, 2, Ar—H), 7.39 (s, 4, CH$_3$PheH).

Compound 13ab was prepared from 90 mg of 2d and 51 mg of 4-ethylphenyl hydrazine hydrochloride in acetic acid as described for 4a. The product was purified by chromatography, to give 105 mg of 13ab; MS-ESI: [M+H]$^+$ 435.21. NMR (CDCl$_3$) δ 1.10 (d, 6, isoC$_3$H$_7$), 1.27 (t, 3, CH$_3$), 1.42 (t, 3, CH$_3$), 2.72 and 2.93 (2×t, 4, CH$_2$CH$_2$), 3.07 (q, 2, CH$_2$), 3.84 (s, 3, OCH$_3$ and m, 1, CH), 4.44 (q, 2, CH$_2$) 6.28 and 6.80 (2×s, 2, Ar—H), 7.32 and 7.42 (2×dd, 4, C$_2$H$_5$Phe-H).

Compound 13ab was saponified to the carboxylic acid, by heating with NaOH in aqueous ethanol according the method described in example for 4b, to give 92 mg of 13bb; MS-ESI: [M+H]$^+$ 407.11. NMR (DMSO-d$^6$) δ 0.98 (d, 6, isoC$_3$H$_7$), 1.23 (t, 3, C$_2$H$_5$), 2.72 (q, 2, CH$_2$), 2.90 (m, 4, 2×CH$_2$CH$_2$), 3.75 (s, 3, OCH$_3$), 3.75 (m, 1, CH), 6.10 and 7.0 (2×m, 2, Ar—H), 7.43 (bs, 4, C$_2$H$_5$Phe-H).

The carboxylic acid was converted into the amide by reaction with N-methyl-N-tert-butylamine according to the method described for 4d, to provide 97 mg of 13cb; MS-ESI: [M+H]$^+$ 476.18. NMR (DMSO-d$^6$) δ 1.00 (d, 6, isoC$_3$H$_7$), 1.22 (t, 3, CH$_3$), 1.43 (s, 9, tertC$_4$H$_9$), 2.70 (m, 4, CH$_2$ and CH$_2$CH$_3$) and 2.86 (m, 2, CH$_2$), 3.02 (s, 3, NCH$_3$), 3.73 (s, 3, OCH$_3$), 3.78 (m, 1, CH), 6.15 and 6.99 (2×s, 2, Ar—H), 7.42 (s, 4, C$_2$H$_5$PheH).

Compound 13ac was prepared from 90 mg of 2d and 53 mg of 4-methoxyphenyl hydrazine hydrochloride in acetic acid as described for 4a. The product was purified by chromatography, to give 71 mg of 13ac; MS-ESI: [M+H]$^+$ 437.18. NMR (CDCl$_3$) δ 1.12 (d, 6, isoC$_3$H$_7$), 1.42 (t, 3, CH$_3$), 2.92 and 3.07 (2×t, 4, CH$_2$CH$_2$), 3.85 and 3.87 (2×s, 6, 2×OCH$_3$), 3.91 (m, 1, CH), 4.43 (q, 2, CH$_2$) 6.28 and 6.80 (2×s, 2, Ar—H), 7.0 and 7.43 (2×dd, 4, CH$_3$OPhe-H).

Compound 13ac was saponified to the carboxylic acid, by heating with NaOH in aqueous ethanol according the method described in example for 4b, to give 58 mg of 13bc; MS-ESI: [M+H]$^+$ 409.10. NMR (DMSO-d$^6$) δ 1.00 (d, 6, isoC$_3$H$_7$), 2.90 (m, 4, 2×CH$_2$CH$_2$), 3.74 and 3.83 (2×s, 6, 2×OCH$_3$), 3.83 (m, 1, CH), 6.11 and 6.98 (2×s, 2, Ar—H), 7.13 and 7.45 (2×d, 4, CH$_3$OPhe-H).

The carboxylic acid was converted into the amide by reaction with N-methyl-N-tert-butylamine according to the method described for 4d, to provide 67 mg of 13 cc; MS-ESI: [M+H]$^+$ 478.16. NMR (DMSO-d$^6$) δ 1.00 (d, 6, isoC$_3$H$_7$), 1.43 (s, 9, tertC$_4$H$_9$), 2.41 (s, 3, CH$_3$), 2.70 and 2.86 (2×m, 4, CH$_2$CH$_2$), 3.02 (s, 3, NCH$_3$), 3.75 (s, 3, OCH$_3$), 3.83 (m, 1, CH), 6.14 and 6.99 (2×s, 2, Ar—H), 7.12 and 7.42 (2×d, 4, CH$_3$OPheH).

Compound 13ad was prepared from 90 mg of 2d and 50 mg of 4-fluorophenyl hydrazine hydrochloride in acetic acid as described for 4a. The product was purified by chromatography, to give 98 mg of 13ad; NMR (CDCl$_3$) δ 1.12 (d, 6, isoC$_3$H$_7$), 1.42 (t, 3, CH$_3$), 2.92 and 3.07 (2×t, 4, CH$_2$CH$_2$), 3.87 (s, 3, OCH$_3$), 3.91 (m, 1, CH), 4.45 (q, 2, CH$_2$) 6.25 and 6.82 (2×s, 2, Ar—H), 7.20 and 7.53 (2×m, 4, F-Phe-H).

Compound 13ad was saponified to the carboxylic acid, by heating with NaOH in aqueous ethanol according the method described in example for 4b, to give 83 mg of 13bd; MS-ESI: [M+H]$^+$ 397.12. NMR (DMSO-d6) δ 1.02 (d, 6, isoC$_3$H$_7$), 2.90 (m, 4, 2×CH$_2$CH$_2$), 3.76 (s, 3, OCH$_3$), 3.86 (m, 1, CH), 6.10 and 7.02 (2×s, 2, Ar—H), 7.46 and 7.62 (2×m, 4, FPhe-H). The carboxylic acid was converted into the amide by reaction with N-methyl-N-tert-butylamine according to the method described for 4d, to provide 67 mg of 13cd; MS-ESI: [M+H]$^+$ 466.16. NMR (DMSO-d$^6$) δ 1.02 (d, 6, isoC$_3$H$_7$), 1.44 (s, 9, tertC$_4$H$_9$), 2.70 and 2.88 (2×m, 4, CH$_2$CH$_2$), 3.02 (s, 3, NCH$_3$), 3.76 (s, 3, OCH$_3$), 3.83 (m, 1, CH), 6.16 and 7.01 (2×s, 2, Ar—H), 7.42 and 7.58 (2×m, 4, FPheH).

Compound 13ae was prepared from 90 mg of 2d and 55 mg of 4-chlorophenyl hydrazine hydrochloride in acetic acid as described for 4a. The product was purified by chromatography, to give 88 mg of 13ae; MS-ESI: [M+H]$^+$ 441.11. NMR (CDCl$_3$) δ 1.13 (d, 6, isoC$_3$H$_7$), 1.43 (t, 3, CH$_3$), 2.91 and 3.04 (2×t, 4, CH$_2$CH$_2$), 3.87 (s, 3, OCH$_3$), 3.92 (m, 1, CH), 4.44 (q, 2, CH$_2$) 6.23 and 6.82 (2×s, 2, Ar—H), 7.49 (s, 4, ClPhe-H).

Compound 13ae was saponified to the carboxylic acid, by heating with NaOH in aqueous ethanol according the method described in example for 4b, to give 85 mg of 13be; MS-ESI: [M+H]$^+$ 413.10. NMR (DMSO) δ 1.03 (d, 6, isoC$_3$H$_7$), 2.90 (m, 4, 2×CH$_2$CH$_2$), 3.78 (s, 3, OCH$_3$), 3.87 (m, 1, CH), 6.11 and 7.12 (2×s, 2, Ar—H), 7.59 and 7.86 (2×d, 4, ClPhe-H).

The carboxylic acid was converted into the amide by reaction with N-methyl-N-tert-butylamine according to the method described for 4d, to provide 73 mg of 13ce; MS-ESI: [M+H]$^+$ 482.12. NMR (DMSO-d$^6$) δ 1.03 (d, 6, isoC$_3$H$_7$), 1.44 (s, 9, tertC$_4$H$_9$), 2.69 and 2.87 (2×m, 4, CH$_2$CH$_2$), 3.01 (s, 3, NCH$_3$), 3.77 (s, 3, OCH$_3$), 3.90 (m, 1, CH), 6.17 and 7.02 (2×s, 2, Ar—H), 7.56 and 7.64 (2×d, 4, ClPheH).

Compound 13af was prepared from 90 mg of 2d and 67 mg of 4-bromophenyl hydrazine hydrochloride in acetic acid as described for 4a. The product was purified by chromatography, to give 126 mg of 13af; NMR (CDCl$_3$) δ 1.15 (d, 6, isoC$_3$H$_7$), 1.42 (t, 3, CH$_3$), 2.93 and 3.06 (2×t, 4, CH$_2$CH$_2$), 3.87 (s, 3, OCH$_3$), 3.92 (m, 1, CH), 4.44 (q, 2, CH$_2$) 6.23 and 6.81 (2×s, 2, Ar—H), 7.43 and 7.64 (2×d, 4, BrPhe-H).

Compound 13af was saponified to the carboxylic acid, by heating with NaOH in aqueous ethanol according the method described in example for 4b, to give 117 mg of 13bf; MS-ESI: [M+H]$^+$ 456.99 and 459.01. NMR (DMSO-d$^6$) δ 1.02 (d, 6, isoC$_3$H$_7$), 2.90 (m, 4, 2×CH$_2$CH$_2$), 3.76 (s, 3, OCH$_3$), 3.86 (m, 1, CH), 6.09 and 7.02 (2×s, 2, Ar—H), 7.52 and 7.81 (2×d, 4, BrPhe-H).

The carboxylic acid was converted into the amide by reaction with N-methyl-N-tert-butylamine according to the method described for 4d, to provide 73 mg of 13cf; MS-ESI: [M+H]$^+$ 526.09 and 528.09. NMR (DMSO-d$^6$) δ 1.03 (d, 6, isoC$_3$H$_7$), 1.45 (s, 9, tertC$_4$H$_9$), 2.69 and 2.88 (2×m, 4, CH$_2$CH$_2$), 3.01 (s, 3, NCH$_3$), 3.76 (s, 3, OCH$_3$), 3.90 (m, 1, CH), 6.15 and 7.01 (2×s, 2, Ar—H), 7.50 and 7.79 (2×d, 4, BrPheH).

Example 14
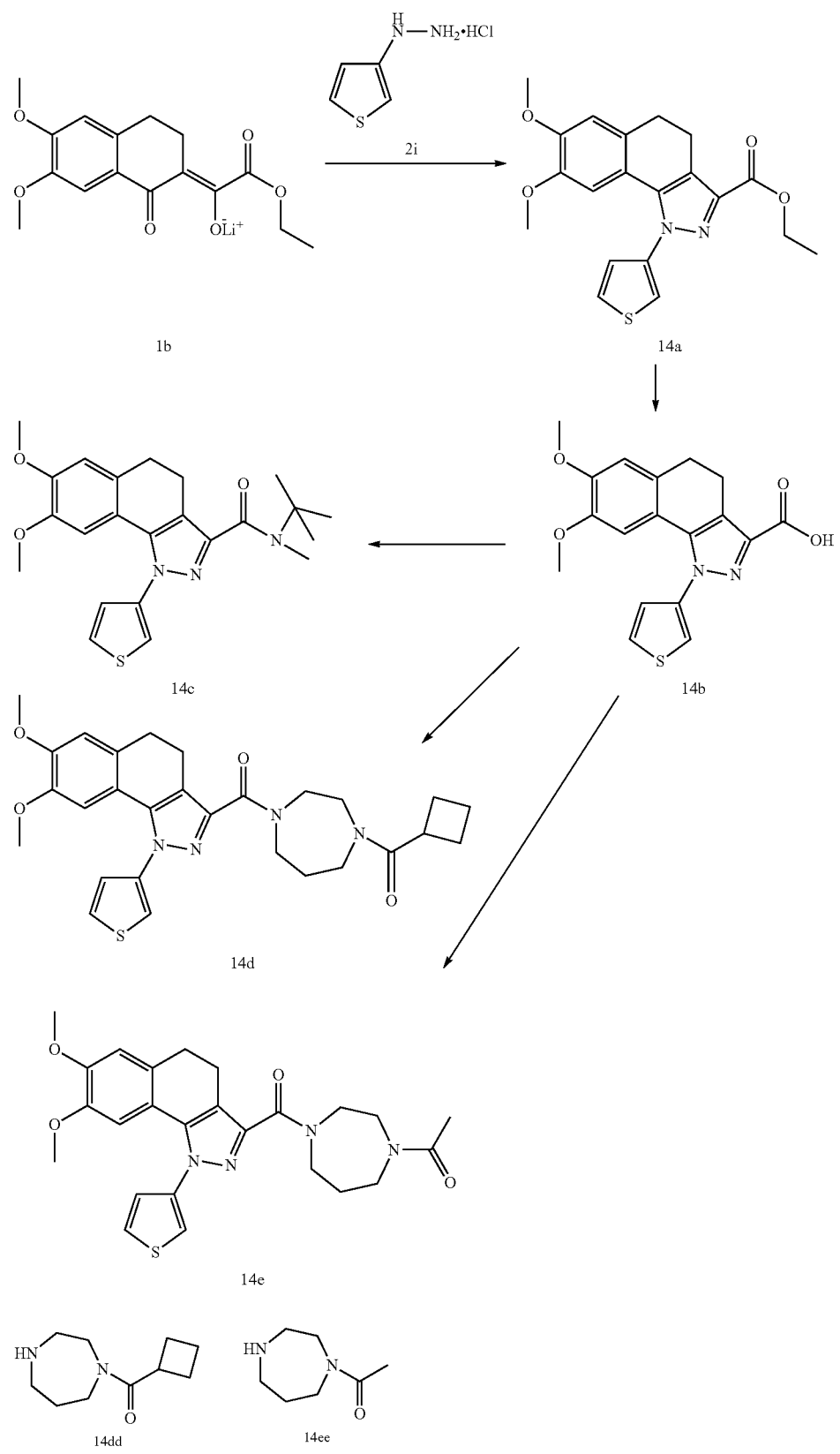

N-tert-butyl-7,8-dimethoxy-N-methyl-1-(thiophen-3-yl)-4,
5-dihydro-1H-benzo[g]indazole-3-carboxamide 14c
(4-(cyclobutanecarbonyl)-1,4-diazepan-1-yl)(7,8-
dimethoxy-1-(thiophen-3-yl)-4,5-dihydro-1H-benzo[g]
indazol-3-yl)methanone 14d
1-(4-(7,8-dimethoxy-1-(thiophen-3-yl)-4,5-dihydro-1H-
benzo[g]indazole-3-carbonyl)-1,4-diazepan-1-yl)etha-
none 14e A mixture of 285 mg of 2i and 500 mg of 1b in 15 ml of abs. ethanol was stirred at RT for 16 hr. The reaction was concentrated to a small volume and the residue was taken up in dichloromethane. The organic material was washed several times with water, dried and concentrated and the crude material purified by chromatography over silica gel, using a gradient of heptane/ethyl acetate, to provide 150 mg of 14a; NMR (CDCl$_3$) δ 1.44 (t, 3, OC$_2$H$_5$), 2.93 and 3.08 (2×m, 4, CH$_2$CH$_2$), 3.51 and 3.90 (2×s, 6, 2×OCH$_3$).

A solution of 150 mg of 14a in 7 ml of dioxane was mixed with 2 ml of 2N NaOH and stirred at 60° C. for 16 hr. The mixture was concentrated and the residue was diluted with water and once washed with ethyl acetate. The aqueous phase was acidified with 1N HCl and the product was extracted with dichloromethane. The organic extract was washed once with water, dried and concentrated, to provide 104 mg of carboxylic acid 14b; R$_f$(CH$_2$Cl$_2$/methanol 9/1) 0.50.

A solution of 70 mg of 14b, 90 mg of HATU, 165 μl of DiPEA and 100 μl of N-methyl-N-tert-butylamine in 3 ml of dichloromethane was stirred at room temperature for 24 hr. The reaction was quenched by addition of 10 ml of 5% aq. citric acid. The product was extracted with dichloromethane. The extract was washed with 5% aq NaHCO$_3$ solution dried and concentrated. The crude product was purified by chromatography over silica gel, using a gradient of toluene/ethyl acetate as eluent. This provided 67 mg of 14c; MS-ESI: [M+H]$^+$ 426.4. NMR (CDCl$_3$) δ 1.53 (s, 9, tertC$_4$H$_9$), 2.86 and 2.93 (2×m, 4, CH$_2$CH$_2$), 3.11 (s, 3, CH$_3$N), 3.51 and 3.90 (2×s, 6, 2×OCH$_3$), 6.42 and 6.81 (2×s, 2, Ar—H), 7.24, 7.45 and 7.49 (3×m, 3,3-thienyl-H).

Similarly, from 70 mg of 14b and 90 mg of cyclobutyl(1,4-diazepan-1-yl)methanone (14dd), 99 mg of 14d were obtained; MS-ESI: [M+H]$^+$ 521.4. NMR (CDCl$_3$) δ 7.47 (m, 2, thiophene-H), 7.23 (m, 1, thiophene-H), 6.81 (2×s, 1, ArH rotamers), 6.46 (2×s, 1, Ar—H, rotamers), 4.04 (m, 1, CH isoC$_3$H$_7$), 3.45-4.02 (m, 8, 4×CH$_2$), 3.88 and 3.53 (2×s, 6, 2×OCH$_3$), 3.30 (m, 1, CH cyclobutyl), 2.88-3.00 (bm, 4, CH$_2$CH$_2$), 2.40-1.80 (4×m, 8, 4×CH$_2$).

Similarly, from 70 mg of 14b and 90 mg of 1-(1,4-diazepan-1-yl)ethanone (14ee), 113 mg of 14e were isolated; MS-ESI: [M+H]$^+$ 481.18. NMR (CDCl$_3$) δ 7.46 (m, 2, thiophene-H), 7.24 (m, 1, thiophene-H), 6.81 (2×s, 1, ArH rotamers), 6.48 (2×s, 1, Ar—H), 3.53-4.10 (m, 8, 4×CH$_2$), 3.89 and 3.52 (2×s, 6, 2×OCH$_3$), 2.88-3.00 (bm, 4, CH$_2$CH$_2$), 2.10-1.88 (bm, 2, CH$_2$). 2.15 (2×s, 3, CH$_3$ rotamers).

Example 15

Agonistic Activity of Compounds at the Human FSH Receptor Expressed in CHO Cells Agonistic activity of the compounds at the human FSH receptor was determined in Chinese Hamster Ovary (CHO) cells stably transfected with the human FSH receptor and cotransfected with a cAMP responsive element (CRE)/promotor directing the expression of a firefly luciferase reporter gene. Binding of the compounds to the Gs protein-coupled FSH receptor will result in an increase of cAMP, which in turn will induce an increased transactivation of the luciferase reporter. Cells (7,500 cells/well of a 384 well plate) were incubated in Dulbecco' minimal essential F12 modified medium (Invitrogen), supplemented with 1 μg/ml bovine insulin, 5 μg/ml human apo-transferrin, 80 U/ml penicillin G and 80 μg/ml streptomycin with the test compounds (concentration between 0.0316 nM and 10.0 μM) in duplicate in a humidified atmosphere (95%) at 5-7% CO$_2$ and 37° C. The final concentration of DMSO was 1%. After 4 hours of incubation, plates were allowed to adjust to room temperature for 1 hour. Then, Luclite (PerkinElmer) solution was added to the wells and cells were allowed to lyse for at least 1 hour at room temperature. Subsequently, luciferase activity was measured in a luminescence counter. The signal is expressed as counts per second (cps). The EC$_{50}$ (concentration of the test compound that elicits half-maximal (50%) luciferase stimulation compared to the compound's maximally attainable effect) and efficacy values (maximal effect of the test compound as percentage of the maximal effect of recombinant human FSH) of the compounds were determined using the software program MathIQ (version 2.0, ID Business Solutions Limited). All compounds showed a pEC$_{50}$ (pEC$_{50}$ is −log EC$_{50}$) of more than 5.

Compounds from examples 1e, 1f, 4d, 7ca, 7cb, 8ca, 9cb, 9cc, 9cd, 10ca, 10cc, 11ga, 12g, 12h, 12ja, 12jb, 12jc, 12jd, 13ca, 13cb, 13 cc, 13cf and 14e exhibited pEC$_{50}$'s in this assay between 5 and 6 (EC$_{50}$ between 10 and 1 μM). Compounds from examples 1g, 6b, 7cc, 7cd, 7cf, 8cb, 8cc, 8cd, 9ca, 10cb, 13cd, 13ce and exhibited pEC$_{50}$'s in this assay 6 and 7 (EC$_{50}$ between 1 μM and 100 nM). Compounds from examples 2h, 2g, 3c, 3d, 5b, 11gb and exhibited pEC$_{50}$'s in this assay above 7 (EC$_{50}$ below 100 nM).

The invention claimed is:

1. A compound according to Formula I

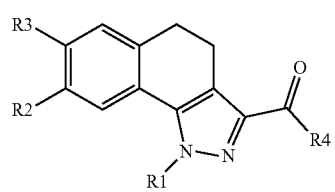

Formula 1 or a pharmaceutically acceptable salt thereof wherein

R1 is phenyl, optionally substituted with halogen, nitro, (1-6C)alkyl, (2-6C)alkenyl, (1-6C)alkoxy, (2-5C)heteroaryl, (3-6C)cycloalkyl; or R1 is (2-5C)heteroaryl, optionally fused with a benzo group and optionally substituted at the heteroaryl or benzo group with halogen or (1-4C)alkyl; or R1 is (2-5C)heterocycloalkyl or (2-5C)heterocycloalkenyl, both optionally substituted with one or more fluorines, (1-2C)alkyl groups or (1-3C)alkoxy groups;

R2 is (1-6C)alkyl, (2-6C)alkenyl, (2-6C)alkynyl, (1-6C)alkoxy or (1-4C)alkylsulfonamino, all alkyl groups optionally substituted with one or more hydroxyl or fluorines; or R2 is (2-5C)heteroaryl, R5-carbonylamino or R5-aminocarbonyl R3 (1-6C)alkoxy or hydroxyl;

R4 is (di)[(1-6C)alkyl]amino; or R4 is pyrrolidin-1-yl, optionally substituted with one or more (1-2C)alkyl groups; or R4 is diazacycloheptyl, optionally substituted with (1-6C)alkylcarbonyl or (3-6C)cycloalkylcarbonyl; or R4 is

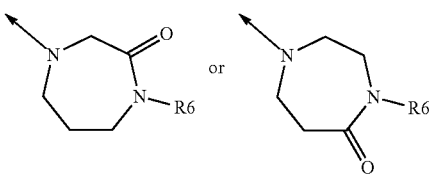

R5 is (2-5C)heteroaryl or (1-6C)alkyl, both optionally substituted with one or more hydroxyl groups or halogens; or R5 is (2-5C)heterocycloalkyl(1-4C)alkyl, the heterocycloalkyl group optionally substituted with (1-4C)alkyl or (di)[(1-4C)alkyl]amino(1-4C)alkyl; and R6 is (1-6C)alkyl.

2. The compound according to claim 1 wherein R2 is (1-6C)alkoxy, (2-5C)heteroaryl, R5-carbonylamino or (1-4C)alkylsulfonamino.

3. The compound according to claim 2 wherein R2 is (1-4C)alkoxy.

4. The compound according to claim 1 wherein R3 is methoxy.

5. The compound according to claim 1 wherein R4 is 1,4-diazacycloheptyl, optionally substituted at the nitrogen at position 4 with (1-6C)alkylcarbonyl or (3-6C)cycloalkylcarbonyl.

6. The compound according to claim 1 wherein R4 is di[(1-6C)alkyl]amino.

7. The compound according to claim 1 wherein R1 is phenyl, optionally substituted with halogen, nitro, (1-6C)alkyl, (2-6C)alkenyl, (1-6C)alkoxy, (3-6C)cycloalkyl or R1 is thienyl.

8. A pharmaceutical composition made by combining a compound according to claim 1, or a pharmaceutically acceptable salt thereof and one or more pharmaceutically acceptable excipients.

9. A pharmaceutical composition according to claim 8, which further comprises at least one additional therapeutically active agent, wherein the additional therapeutic agent is a gonadotropin agonist or a GnRH modulator.

10. A method of ovarian stimulation comprising administering a therapeutically effective amount of a compound according to claim 1 to a patient in need thereof.

11. A method of treating a fertility disorder comprising administering a therapeutically effective amount of a compound according to claim 1 to a patient in need thereof.

* * * * *